United States Patent
Shin et al.

(10) Patent No.: US 7,592,168 B2
(45) Date of Patent: Sep. 22, 2009

(54) CEPHALOSPORIN C ACYLASE MUTANT AND METHOD FOR PREPARING 7-ACA USING SAME

(75) Inventors: Yong Chul Shin, Jinju-si (KR); John Y J Jeon, Seoul (KR); Kyung Hwa Jung, Jinju-si (KR); Mi Ran Park, Busan (KR); Youngso Kim, Seoul (KR)

(73) Assignee: Sandoz AG, Basel (CH)

( * ) Notice: Subject to any disclaimer, the term of this patent is extended or adjusted under 35 U.S.C. 154(b) by 232 days.

(21) Appl. No.: 10/568,132

(22) PCT Filed: Aug. 10, 2004

(86) PCT No.: PCT/KR2004/002005

§ 371 (c)(1), (2), (4) Date: Oct. 19, 2006

(87) PCT Pub. No.: WO2005/014821

PCT Pub. Date: Feb. 17, 2005

(65) Prior Publication Data

US 2007/0207519 A1    Sep. 6, 2007

(30) Foreign Application Priority Data

Aug. 11, 2003    (KR) .................. 10-2003-0055259

(51) Int. Cl.
*C12N 9/80* (2006.01)
*C07H 21/04* (2006.01)
(52) U.S. Cl. ..................... 435/228; 536/23.2
(58) Field of Classification Search .............. 435/228; 536/23.2
See application file for complete search history.

(56) References Cited

U.S. PATENT DOCUMENTS

| | | | |
|---|---|---|---|
| 4,774,179 A | 9/1988 | Ichikawa | |
| 5,104,800 A | 4/1992 | Crawford | |
| 5,168,048 A | 12/1992 | Quax | |
| 5,192,678 A | 3/1993 | Iwami | |
| 5,229,274 A | 7/1993 | Crawford | |
| 5,320,948 A | 6/1994 | Iwami | |
| 5,336,613 A * | 8/1994 | Niwa et al. ............. | 435/228 |
| 5,354,667 A | 10/1994 | Croux | |
| 5,457,032 A | 10/1995 | Quax | |
| 5,677,141 A | 10/1997 | Isogai | |
| 5,695,978 A | 12/1997 | Quax | |
| 5,804,429 A | 9/1998 | Niwa et al. | |
| 5,891,703 A | 4/1999 | Van Der Laan | |
| 5,935,831 A | 8/1999 | Quax | |
| 6,033,823 A * | 3/2000 | Van Der Laan et al. ...... | 430/230 |
| 6,297,032 B1 | 10/2001 | Ramsden | |
| 6,403,356 B1 | 6/2002 | You | |
| 2005/0124029 A1 | 6/2005 | Alkema | |

FOREIGN PATENT DOCUMENTS

| | | |
|---|---|---|
| EP | 1553175 A1 | 1/2005 |
| JP | 60110292 | 11/1983 |
| JP | 61152286 | 12/1984 |
| JP | 62048379 | 8/1985 |
| JP | 62048380 | 8/1985 |
| JP | 04104792 | 8/1990 |
| JP | 07222587 | 2/1994 |
| JP | 08098686 | 10/1994 |
| JP | 08205864 | 12/1994 |
| WO | WO0272806 | 9/2002 |
| WO | WO03/064613 | 8/2003 |
| WO | WO2005/014821 | 2/2005 |

OTHER PUBLICATIONS

Eur. J. Biochem 269, 2093-2100, Wynand B Alkema, et al "The role of hydrophobic active-site residues in substrate specificity and acyl transfer activity of penicillin acylase", XP-002264819.

Eur. J. Biochem 230, 773-778 (1995) Yoshinori Ishii, et al High Level production, chemical modification and site directed mutagenesis of a cephalosporin C Acylase from Pseudomonas strain N176.

Chemistry and Biology 8 (2001) 1253-1264, Youngsoo Kim, "Structure of cephalosporin acylase in complex with glutaryl-7-aminocephalosporanic acid and glutarate; insight into the basis of its substrate specificity".

Structure, vol. 8, 1059-1068, Oct. 2000, Youngsoo Kim, et al The 2.0 A vrystal structure of cephalosporin acylase.

Annals of the NY Academy of Sciences, vol. 782, 1996, pp. 226-240, Yoshimasa Saito et al:"protein Engineering of a Cephalosporin C Acylase from Pseudomonas Strain N176".

Protein Engineering, vol. 13, No. 12, 2000, pp. 857-863, Wynand B.L. Alkema et al: "Characterization of the beta-lactam Binding Site of Penicillin Acylase of *Escheriarchia coli* by Structural and Site-Directed Mutagenesis Studies".

The journal of Biological Chemistry, vol. 277, No. 44, Nov. 2002, pp. 42121-42127, Linda G. Otten et al:"Altering the Substrate Specificity of Cephalosporin Acylase by Directed Evolution of the beta-subunit".

(Continued)

*Primary Examiner*—Tekchand Saidha
(74) *Attorney, Agent, or Firm*—Jeffrey S. Melcher; Manelli Denison & Selter, PLLC

(57) ABSTRACT

A CPC acylase mutant of the present invention has an improved reactivity and specific activity to CPC, which can be efficiently employed for directly preparing 7-ACA from CPC by a one-step enzymatic method.

17 Claims, 12 Drawing Sheets

OTHER PUBLICATIONS

Matsuda, et. al., J. Bacteriol, 169, pp. 5821-5829 (1987), discussed on p. 2 of the present application.

Aramori, et. al., J. Ferment. Bioeng. 72, pp. 232-243, (1991), discussed on p. 2 of the present application.

Li, et. al., Eur. J. Biochem. 262, pp. 713-719 (1999), discussed on p. 2 of the present application.

Kim, et. al., J. Biol. Chem. 276, pp. 48376-48381 (2001), discussed on p. 2 of the present application.

Kim, et. al., Biotech. Lett. 23, pp. 1067-1071 (2001), discussed on p. 3 of the present application.

* cited by examiner

SEQUENCE LISTING

```
<160> NUMBER OF SEQ ID NOS: 46

<210> SEQ ID NO 1
<211> LENGTH: 2325
<212> TYPE: DNA
<213> ORGANISM: Artificial Sequence
<220> FEATURE:
<223> OTHER INFORMATION: Synthesized wild-type CPC acylase acyII gene

<400> SEQUENCE: 1
atgaccatgg cggcgaaaac cgatcgtgaa gcgctgcagg cggcgctgcc gccgctgagc      60
ggcagcctga gcatcccggg cctgagcgcg ccggtgcgtg tgcagcgtga tggctggggc     120
atcccgcata tcaaagcgag cggcgaagcg gatgcgtatc gtgcgttggg ctttgtgcat     180
gcgcaggatc gtctgtttca gatggaactg acccgtcgta aagcgctggg ccgtgcggcg     240
gaatggctgg gcgcggaagc ggcggaagcg gatatcctgg tgcgtcgtct gggcatggaa     300
aaagtgtgcc gtcgtgattt tgaagcgctg ggcgcggaag cgaaagatat gctgcgtgcg     360
tatgtggcgg gcgtgaacgc gtttctggcg agcgcgcgc cgctgccgat cgaatatggc     420
ctgctgggcg cggaaccgga accgtgggaa ccgtggcata gcatcgcggt gatgcgtcgt     480
ctgggcctgc tgatgggcag cgtgtggttt aaactgtggc gtatgctggc gctgccggtg     540
gtgggcgcgg cgaacgcgct gaaactgcgt tatgatgatg gcggccagga tctgctgtgc     600
atcccgccgg gcgtggaagc ggaacgtctg gaagcggatc tggcggcgct gcgtccgcgg     660
gtggatgcgc tgctgaaagc gatgggcggc gatgcgagcg atgcggcggg cggcggcagc     720
```

-continued

```
aacaactggg cggtggcgcc gggccgtacc gcgaccggcc gtccgatcct ggcgggcgat      780
ccgcatcgtg tgtttgaaat cccgggcatg tatgcgcagc atcatctggc gtgcgatcgt      840
tttgatatga tcggcctgac cgtgccgggc gtgccgggct tccgcatttt tgcgcataac      900
ggcaaagtgg cgtattgcgt gacccatgcg tttatggata tccatgatct gtatctggaa      960
cagtttgcgg aagatggccg taccgcgcgt tttggcaacg aatttgaacc ggtggcgtgg     1020
cgtcgtgatc gtatcgcggt gcgtggcggc gcggatcgtg aatttgatat cgtggaaacc     1080
cgtcatggcc cggtgatcgc gggcgatccg ctggaaggcg cggcgctgac cctgcgtagc     1140
gtgcagtttg cggaaaccga tctgagcttt gattgcctga cccgtatgcc gggcgcgagc     1200
accgtggcgc agctgtatga tgcgacccgt ggctggggcc tgatcgatca taacctggtg     1260
gcgggcgatg tggcgggcag catcggccat ctggtgcgtg cgcgtgtgcc gagccgtccg     1320
cgtgaaaacg gctggctgcc ggtgccgggc tggagcggcg aacatgaatg cgtggctgg      1380 attccgcatg aagcgatgcc gcgtgtgatc gatccgccgg gcggcctgat cgtgaccgcg     1440
aacaaccgtg tggtggcgga tgatcatccg gattatctgt gcaccgattg ccatccgccg     1500
tatcgtgcgg aacgtatcat ggaacgtctg gtggcgagcc cggcgtttgc ggtggatgat     1560
gcggcggcga tccatgcgga taccctgagc ccgcatgtgg ccctgctgcg tgcgcgtctg     1620
gaagcgctgg catccaggg cagcctgccg gcggaagaac tgcgtcagac cctgatcgcg     1680
tgggatggcc gtatgatgc gggcagccag gcggcgagcg cgtataacgc gtttcgtcgt     1740
gcgctgaccc gtctggtgac cgcgcgtagc ggcctggaac aggcgatcgc gcatccgttt     1800
gcggcggtgc cgccgggcgt gagcccgcag ggccaggtgt ggtgggcggt gccgaccctg     1860
ctgcgtaacg atgatgcggg catgctgaaa ggctggagct gggatgaagc gctgagcgaa     1920
gcgctgagcg tggcgaccca gaacctgacc ggccgtggct ggggcgaaga acatcgtccg     1980 cgtttaccc atccgctgag cgcgcagttt ccggcgtggg cggcgctgct gaacccggtg     2040
agccgtccga tcggcggcga tggcgatacc gtgctagcga acggcctggt gccgagcgcg     2100
ggcccggaag cgacttatgg cgcgctgagc cgttatgtgt ttgatgtggg caactgggat     2160
aacagccgtt gggtggtgtt tcatggcgcg agcggccatc cggcgagccc gcattatgcg     2220
gatcagaacg cgccgtggag cgattgcgcg atggtgccga tgctgtatag ctgggatcgt     2280
atcgcggcgg aagcggtgac cagccaggaa ctggtgccgg cgtaa                     2325
```

<210> SEQ ID NO 2
<211> LENGTH: 774
<212> TYPE: PRT
<213> ORGANISM: Pseudomonas sp. SE83

<400> SEQUENCE: 2

```
Met Thr Met Ala Ala Lys Thr Asp Arg Glu Ala Leu Gln Ala Leu
  1               5                  10                  15

Pro Pro Leu Ser Gly Ser Leu Ser Ile Pro Gly Leu Ser Ala Pro Val
                 20                  25                  30

Arg Val Gln Arg Asp Gly Trp Gly Ile Pro His Ile Lys Ala Ser Gly
             35                  40                  45

Glu Ala Asp Ala Tyr Arg Ala Leu Gly Phe Val His Ala Gln Asp Arg
         50                  55                  60

Leu Phe Gln Met Glu Leu Thr Arg Arg Lys Ala Leu Gly Arg Ala Ala
     65                  70                  75                  80

Glu Trp Leu Gly Ala Glu Ala Ala Glu Ala Asp Ile Leu Val Arg Arg
```

-continued

```
                     85                  90                  95
Leu Gly Met Glu Lys Val Cys Arg Arg Asp Phe Glu Ala Leu Gly Ala
                100                 105                 110
Glu Ala Lys Asp Met Leu Arg Ala Tyr Val Ala Gly Val Asn Ala Phe
            115                 120                 125
Leu Ala Ser Gly Ala Pro Leu Pro Ile Glu Tyr Gly Leu Leu Gly Ala
        130                 135                 140
Glu Pro Glu Pro Trp Glu Pro Trp His Ser Ile Ala Val Met Arg Arg
145                 150                 155                 160
Leu Gly Leu Leu Met Gly Ser Val Trp Phe Lys Leu Trp Arg Met Leu
                165                 170                 175
Ala Leu Pro Val Val Gly Ala Ala Asn Ala Leu Lys Leu Arg Tyr Asp
            180                 185                 190
Asp Gly Gly Gln Asp Leu Leu Cys Ile Pro Pro Gly Val Glu Ala Glu
        195                 200                 205
Arg Leu Glu Ala Asp Leu Ala Ala Leu Arg Pro Ala Val Asp Ala Leu
    210                 215                 220
Leu Lys Ala Met Gly Gly Asp Ala Ser Asp Ala Ala Gly Gly Gly Ser
225                 230                 235                 240
Asn Asn Trp Ala Val Ala Pro Gly Arg Thr Ala Thr Gly Arg Pro Ile
                245                 250                 255
Leu Ala Gly Asp Pro His Arg Val Phe Glu Ile Pro Gly Met Tyr Ala
            260                 265                 270
Gln His His Leu Ala Cys Asp Arg Phe Asp Met Ile Gly Leu Thr Val
        275                 280                 285
Pro Gly Val Pro Gly Phe Pro His Phe Ala His Asn Gly Lys Val Ala
    290                 295                 300
Tyr Cys Val Thr His Ala Phe Met Asp Ile His Asp Leu Tyr Leu Glu
305                 310                 315                 320
Gln Phe Ala Glu Asp Gly Arg Thr Ala Arg Phe Gly Asn Glu Phe Glu
                325                 330                 335
Pro Val Ala Trp Arg Arg Asp Arg Ile Ala Val Arg Gly Gly Ala Asp
            340                 345                 350
Arg Glu Phe Asp Ile Val Glu Thr Arg His Gly Pro Val Ile Ala Gly
        355                 360                 365
Asp Pro Leu Glu Gly Ala Ala Leu Thr Leu Arg Ser Val Gln Phe Ala
    370                 375                 380
Glu Thr Asp Leu Ser Phe Asp Cys Leu Thr Arg Met Pro Gly Ala Ser
385                 390                 395                 400
Thr Val Ala Gln Leu Tyr Asp Ala Thr Arg Gly Trp Gly Leu Ile Asp
                405                 410                 415
His Asn Leu Val Ala Gly Asp Val Ala Gly Ser Ile Gly His Leu Val
            420                 425                 430
Arg Ala Arg Val Pro Ser Arg Pro Arg Glu Asn Gly Trp Leu Pro Val
        435                 440                 445
Pro Gly Trp Ser Gly Glu His Glu Trp Arg Gly Trp Ile Pro His Glu
    450                 455                 460
Ala Met Pro Arg Val Ile Asp Pro Pro Gly Gly Leu Ile Val Thr Ala
465                 470                 475                 480
Asn Asn Arg Val Val Ala Asp Asp His Pro Asp Tyr Leu Cys Thr Asp
                485                 490                 495
Cys His Pro Pro Tyr Arg Ala Glu Arg Ile Met Glu Arg Leu Val Ala
            500                 505                 510
```

```
Ser Pro Ala Phe Ala Val Asp Asp Ala Ala Ile His Ala Asp Thr
        515                 520                 525

Leu Ser Pro His Val Gly Leu Leu Arg Ala Arg Leu Glu Ala Leu Gly
        530                 535                 540

Ile Gln Gly Ser Leu Pro Ala Glu Glu Leu Arg Gln Thr Leu Ile Ala
545                 550                 555                 560

Trp Asp Gly Arg Met Asp Ala Gly Ser Gln Ala Ser Ala Tyr Asn
                565                 570                 575

Ala Phe Arg Arg Ala Leu Thr Arg Leu Val Thr Ala Arg Ser Gly Leu
                580                 585                 590

Glu Gln Ala Ile Ala His Pro Phe Ala Ala Val Pro Pro Gly Val Ser
        595                 600                 605

Pro Gln Gly Gln Val Trp Trp Ala Val Pro Thr Leu Leu Arg Asn Asp
        610                 615                 620

Asp Ala Gly Met Leu Lys Gly Trp Ser Trp Asp Glu Ala Leu Ser Glu
625                 630                 635                 640

Ala Leu Ser Val Ala Thr Gln Asn Leu Thr Gly Arg Gly Trp Gly Glu
                645                 650                 655

Glu His Arg Pro Arg Phe Thr His Pro Leu Ser Ala Gln Phe Pro Ala
        660                 665                 670

Trp Ala Ala Leu Leu Asn Pro Val Ser Arg Pro Ile Gly Gly Asp Gly
        675                 680                 685

Asp Thr Val Leu Ala Asn Gly Leu Val Pro Ser Ala Gly Pro Glu Ala
        690                 695                 700

Thr Tyr Gly Ala Leu Ser Arg Tyr Val Phe Asp Val Gly Asn Trp Asp
705                 710                 715                 720

Asn Ser Arg Trp Val Val Phe His Gly Ala Ser Gly His Pro Ala Ser
                725                 730                 735

Pro His Tyr Ala Asp Gln Asn Ala Pro Trp Ser Asp Cys Ala Met Val
        740                 745                 750

Pro Met Leu Tyr Ser Trp Asp Arg Ile Ala Ala Glu Ala Val Thr Ser
        755                 760                 765

Gln Glu Leu Val Pro Ala
        770

<210> SEQ ID NO 3
<211> LENGTH: 2334
<212> TYPE: DNA
<213> ORGANISM: Artificial Sequence
<220> FEATURE:
<223> OTHER INFORMATION: wild-type CPC acylase sem gene

<400> SEQUENCE: 3
atgaccatgg cggcgaaaac tgatcgtgaa gcgctgcagg cggcgctgcc gccgctgagc      60
ggcagcctga gcatcccggg cctgagcgcg ccggtgcgtg tgcagcgtga tggctggggc     120
atcccgcata tcaaagcgag cggcgaagcg gatgcgtatc gtgcgttggg ctttgtgcat     180
gcgcaggatc gtctgtttca gatggaactg accgtcgta aagcgctggg ccgtgcggcg      240
gaatggctgg gcgcggaagc ggcggaagcg gatatcctgg tgcgtcgtct gggcatggaa     300
aaagtgtgcc gtcgtgattt tgaagcgctg gcgcgaaag cgaaagatat gctgcgtgcg      360
tatgtggcgg gcgtgaacgc gtttctggcg agcggcgcgc cgctgccgat cgaatatggc     420
ctgctgggcg cggaaccgga accgtgggaa ccgtggcata gcatcgcggt gatgcgtcgt     480
ctgggcctgc tgatgggcag cgtgtggttt aaactgtggc gtatgctggc gctgccggtg     540
```

-continued

```
gtgggcgcgg cgaacgcgct gaaactgcgt tatgatgatg gcggccagga tctgctgtgc      600
atcccgccgg gcgtggaagc ggaacgtctg gaagcggatc tggcggcgct gcgtccggcg      660
gtggatgcgc tgctgaaagc gatgggcggc taatgactag tgaattcaag gaggtaataa      720
ataatgagca acaactgggc ggtggcgccg ggccgtaccg cgaccggccg cccgatcctg      780
gcgggcgatc cgcatcgtgt gtttgaaatc ccgggcatgt atgcgcagca tcatctggcg      840
tgcgatcgtt ttgatatgat cggcctgacc gtgccgggcg tgccgggctt ccgcattttt      900
gcgcataacg gcaaagtggc gtattgcgtg acccatgcgt ttatggatat ccatgatctg      960
tatctggaac agtttgcgga gatggccgt accgcgcgtt ttggcaacga atttgaaccg     1020
gtggcttggc gtcgtgatcg tatcgcggtg cgtggcggcg cggatcgtga atttgatatc     1080
gtggaaaccc gtcatggccc ggtgatcgcg ggcgatccgc tggaaggcgc ggcgctgacc     1140
ctgcgtagcg tgcagtttgc ggaaaccgat ctgagctttg attgcctgac cgtatgccg      1200
ggcgcgagca ccgtggcgca gctgtatgat gcgacccgtg gctgggcct gatcgatcat      1260
aacctggtgg cgggcgatgt ggcgggcagc atcggccatc tggtgcgtgc gcgtgtgccg     1320
agccgtccgc gtgaaaacgg ctggctgccg gtgccgggct ggagcggcga acatgaatgg     1380
cgtggctgga ttccgcatga agcgatgccg cgtgtgatcg atccgccggg cggcctgatc     1440
gtgaccgcga acaaccgtgt ggtggcggat gatcatccgg attatctgtg caccgattgc     1500
catccgccgt atcgtgcgga acgtatcatg aacgtctgg tggcgagccc ggcgtttgcg      1560
gtggatgatg cggcggcgat ccatgcggat accctgagcc gcatgtgggc ctgctgcgt     1620
gcgcgtctgg aagctttggg catccagggc agcctgccgg cggaagaact gcgtcagacc     1680
ctgatcgcgt gggatggccg tatggatgcg ggcagccagg cggcgagcgc gtataacgcg     1740
tttcgtcgtg cgctgacccg tctggtgacc gcgcgtagcg gcctggaaca ggcgatcgcg     1800
catccgtttg cggcggtgcc gccgggcgtg agcccgcagg gccaggtgtg gtgggcggtg     1860
ccgaccctgc tgcgtaacga tgatgcgggc atgctgaaag ctggagctg gatgaagcg      1920
ctgagcgaag cgctgagcgt ggcgacccag aacctgaccg gccgtggctg gggcgaagaa     1980
catcgtccgc gttttaccca tccgctgagc gcgcagtttc cggcgtgggc ggcgctgctg     2040
aacccggtga gccgtccgat cggcggcgat ggcgataccg tgctagcgaa cggcctggtg     2100
ccgagcgcgg gcccggaagc gacttatggc gcgctgagcc gttatgtgtt tgatgtgggc     2160
aactgggata cagccgttg gtggtgtttt catggcgcga gcggccatcc ggcgagcccg     2220
cattatgcgg atcagaacgc gccgtggagc gattgcgcga tggtgccgat gctgtatagc     2280
tgggatcgta tcgcggcgga agcggtgacc agccaggaac tggtgccggc gtaa          2334
```

<210> SEQ ID NO 4
<211> LENGTH: 229
<212> TYPE: PRT
<213> ORGANISM: Pseudomonas sp. SE83

<400> SEQUENCE: 4

```
Thr Met Ala Ala Lys Thr Asp Arg Glu Ala Leu Gln Ala Ala Leu Pro
  1               5                  10                  15

Pro Leu Ser Gly Ser Leu Ser Ile Pro Gly Leu Ser Ala Pro Val Arg
             20                  25                  30

Val Gln Arg Asp Gly Trp Gly Ile Pro His Ile Lys Ala Ser Gly Glu
         35                  40                  45

Ala Asp Ala Tyr Arg Ala Leu Gly Phe Val His Ala Gln Asp Arg Leu
```

-continued

```
                50                  55                  60
Phe Gln Met Glu Leu Thr Arg Arg Lys Ala Leu Gly Arg Ala Ala Glu
 65                  70                  75                  80

Trp Leu Gly Ala Glu Ala Glu Ala Asp Ile Leu Val Arg Arg Leu
                 85                  90                  95

Gly Met Glu Lys Val Cys Arg Arg Asp Phe Glu Ala Leu Gly Ala Glu
                100                 105                 110

Ala Lys Asp Met Leu Arg Ala Tyr Val Ala Gly Val Asn Ala Phe Leu
                115                 120                 125

Ala Ser Gly Ala Pro Leu Pro Ile Glu Tyr Gly Leu Leu Gly Ala Glu
130                 135                 140

Pro Glu Pro Trp Glu Pro Trp His Ser Ile Ala Val Met Arg Arg Leu
145                 150                 155                 160

Gly Leu Leu Met Gly Ser Val Trp Phe Lys Leu Trp Arg Met Leu Ala
                165                 170                 175

Leu Pro Val Val Gly Ala Ala Asn Ala Leu Lys Leu Arg Tyr Asp Asp
                180                 185                 190

Gly Gly Gln Asp Leu Leu Cys Ile Pro Pro Gly Val Glu Ala Glu Arg
                195                 200                 205

Leu Glu Ala Asp Leu Ala Ala Leu Arg Pro Ala Val Asp Ala Leu Leu
        210                 215                 220

Lys Ala Met Gly Gly
225

<210> SEQ ID NO 5
<211> LENGTH: 535
<212> TYPE: PRT
<213> ORGANISM: Pseudomonas sp. SE83

<400> SEQUENCE: 5

Ser Asn Asn Trp Ala Val Ala Pro Gly Arg Thr Ala Thr Gly Arg Pro
  1               5                  10                  15

Ile Leu Ala Gly Asp Pro His Arg Val Phe Glu Ile Pro Gly Met Tyr
                 20                  25                  30

Ala Gln His His Leu Ala Cys Asp Arg Phe Asp Met Ile Gly Leu Thr
             35                  40                  45

Val Pro Gly Val Pro Gly Phe Pro His Phe Ala His Asn Gly Lys Val
         50                  55                  60

Ala Tyr Cys Val Thr His Ala Phe Met Asp Ile His Asp Leu Tyr Leu
 65                  70                  75                  80

Glu Gln Phe Ala Glu Asp Gly Arg Thr Ala Arg Phe Gly Asn Glu Phe
                 85                  90                  95

Glu Pro Val Ala Trp Arg Arg Asp Arg Ile Ala Val Arg Gly Gly Ala
                100                 105                 110

Asp Arg Glu Phe Asp Ile Val Glu Thr Arg His Gly Pro Val Ile Ala
                115                 120                 125

Gly Asp Pro Leu Glu Gly Ala Ala Leu Thr Leu Arg Ser Val Gln Phe
130                 135                 140

Ala Glu Thr Asp Leu Ser Phe Asp Cys Leu Thr Arg Met Pro Gly Ala
145                 150                 155                 160

Ser Thr Val Ala Gln Leu Tyr Asp Ala Thr Arg Gly Trp Gly Leu Ile
                165                 170                 175

Asp His Asn Leu Val Ala Gly Asp Val Ala Gly Ser Ile Gly His Leu
                180                 185                 190
```

Val Arg Ala Arg Val Pro Ser Arg Pro Arg Glu Asn Gly Trp Leu Pro
        195                 200                 205

Val Pro Gly Trp Ser Gly Glu His Glu Trp Arg Gly Trp Ile Pro His
    210                 215                 220

Glu Ala Met Pro Arg Val Ile Asp Pro Gly Gly Leu Ile Val Thr
225                 230                 235                 240

Ala Asn Asn Arg Val Val Ala Asp Asp His Pro Asp Tyr Leu Cys Thr
                245                 250                 255

Asp Cys His Pro Pro Tyr Arg Ala Glu Arg Ile Met Glu Arg Leu Val
            260                 265                 270

Ala Ser Pro Ala Phe Ala Val Asp Ala Ala Ala Ile His Ala Asp
        275                 280                 285

Thr Leu Ser Pro His Val Gly Leu Leu Arg Ala Arg Leu Glu Ala Leu
        290                 295                 300

Gly Ile Gln Gly Ser Leu Pro Ala Glu Glu Leu Arg Gln Thr Leu Ile
305                 310                 315                 320

Ala Trp Asp Gly Arg Met Asp Ala Gly Ser Gln Ala Ala Ser Ala Tyr
                325                 330                 335

Asn Ala Phe Arg Arg Ala Leu Thr Arg Leu Val Thr Ala Arg Ser Gly
            340                 345                 350

Leu Glu Gln Ala Ile Ala His Pro Phe Ala Ala Val Pro Pro Gly Val
        355                 360                 365

Ser Pro Gln Gly Gln Val Trp Trp Ala Val Pro Thr Leu Leu Arg Asn
    370                 375                 380

Asp Asp Ala Gly Met Leu Lys Gly Trp Ser Trp Asp Glu Ala Leu Ser
385                 390                 395                 400

Glu Ala Leu Ser Val Ala Thr Gln Asn Leu Thr Gly Arg Gly Trp Gly
                405                 410                 415

Glu Glu His Arg Pro Arg Phe Thr His Pro Leu Ser Ala Gln Phe Pro
            420                 425                 430

Ala Trp Ala Ala Leu Leu Asn Pro Val Ser Arg Pro Ile Gly Gly Asp
        435                 440                 445

Gly Asp Thr Val Leu Ala Asn Gly Leu Val Pro Ser Ala Gly Pro Glu
    450                 455                 460

Ala Thr Tyr Gly Ala Leu Ser Arg Tyr Val Phe Asp Val Gly Asn Trp
465                 470                 475                 480

Asp Asn Ser Arg Trp Val Val Phe His Gly Ala Ser Gly His Pro Ala
                485                 490                 495

Ser Pro His Tyr Ala Asp Gln Asn Ala Pro Trp Ser Asp Cys Ala Met
            500                 505                 510

Val Pro Met Leu Tyr Ser Trp Asp Arg Ile Ala Ala Glu Ala Val Thr
        515                 520                 525

Ser Gln Glu Leu Val Pro Ala
    530                 535

<210> SEQ ID NO 6
<211> LENGTH: 2325
<212> TYPE: DNA
<213> ORGANISM: Artificial Sequence
<220> FEATURE:
<223> OTHER INFORMATION: mutant CPC acylase S12 gene

<400> SEQUENCE: 6
atgaccatgg cggcgaaaac tgatcgtgaa gcgctgcagg cggcgctgcc gccgctgagc      60
ggcagcctga gcatcccggg cctgagcgcg ccggtgcgtg tgcagcgtga tggctggggc     120

-continued

```
atcccgcata tcaaagcgag cggcgaagcg gatgcgtatc gtgcgttggg ctttgtgcat      180
gcgcaggatc gtctgtttca gatggaactg acccgtcgta aagcgctggg ccgtgcggcg      240
gaatggctgg gcgcggaagc ggcggaagcg gatatcctgg tgcgtcgtct gggcatggaa      300
aaagtgtgcc gtcgtgattt tgaagcgctg gcgcggaag cgaaagatat gctgcgtgcg      360
tatgcggcgg gcgtgaacgc gtttctggcg agcggcgcgc cgctgccgat cgaatatagc      420
ctgctgggcg cggaaccgga accgtgggaa ccgtggcata gcatcgcggt gatgcgtcgt      480
ctgggcctgc tgatgggcag cgtgtggttt aaactgtggc gtatgctggc gctgccggtg      540
gtgggcgcgg cgaacgcgct gaaactgcgt tatgatgatg cggccagga tctgctgtgc      600 atcccgccgg gcgtggaagc ggaacgtctg gaagcggatc tggcgcgct gcgtccggcg      660 gtggatgcgc tgctgaaagc gatgggcggc gatgcgagcg atgcggcggg cggcggcagc      720
aacaactggg cggtggcgcc gggccgtacc gcgaccggcc gcccgatcct ggcgggcgat      780
ccgcatcgtg tgtttgaaat cccgggcatg tatgcgcagc atcatctggc gtgcgatcgt      840
tttgatatga tcggcctgac cgtgccgggc gtgccgggct ttccgcataa tgcgcataac      900
ggcaaagtgg cgtattgcgt gacccatgcg tttatggata cccatgatct gtatctggaa      960
cagtttgcgg aagatggccg taccgcgcgt tttggcaacg aatttgaacc ggtggcttgg     1020
cgtcgtgatc gtatcgcggt gcgtggcggc gcggatcgtg aatttgatat cgtggaaacc     1080
cgtcatggcc cggtgatcgc gggcgatccg ctggaaggcg cggcgctgac cctgcgtagc     1140
gtgcagtttg cggaaaccga tctgagcttt gattgcctga cccgtatgcc gggcgcgagc     1200
accgtggcgc agctgtatga tgcgacccgt ggctggggcc tggttgatca taacctggtg     1260
gcgggcgatg tggcgggcag catcggccat ctggtgcgtg cgcgtgtgcc gagccgtccg     1320
cgtgaaaacg gctggctgcc ggtgccgggc tggagcggcg aacatgaatg gcgtggctgg     1380
attccgcatg aagcgatgcc gcgtgtgatc gatccgccgg gcggcctgat cgtgaccgcg     1440
aacaaccgtg tggtggcgga tgatcatccg gattatctgt gcaccgattg ccatccgccg     1500
tatcgtgcgg aacgtatcat ggaacgtctg gtggcgagcc cggcgtttgc ggtggatgat     1560
gcggcggcga tccatgcgga taccctgagc ccgcatgtgg gcctgctgcg tgcgcgtctg     1620
gaagctttgg gcatccaggg cagcctgccg gcggaagaac tgcgtcagac cctgatcgcg     1680
tgggatggcc gtatggatgc gggcagccag gcggcgagcg cgtataacgc gtttcgtcgt     1740
gcgctgaccc gtcggtgac cgcgcgtagc ggcctggaac aggcgatcgc gcatccgttt     1800
gcggcggtgc cgccgggcgt gagcccgcag ggccaggtgt ggtgggcggt gccgacccctg     1860 ctgcgtaacg atgatgcggg catgctgaaa ggctggagct gggatgaagc gctgagcgaa     1920
gcgctgagcg tggcgaccca gaacctgacc ggccgtggct ggggcgaaga acatcgtccg     1980
cgttttaccc atccgctgag cgcgcagttt ccggcgtggg cggcgctgct gaacccggtg     2040
agccgtccga tcggcggcga tggcgatacc gtgctagcga acggcctggt gccgagcgcg     2100
ggcccggaag cgacttatgg cgcgctgtgc cgttatgtgt ttgatgtggg caactgggat     2160
aacagccgtt gggtggtgtt tcatggcgcg agcggccatc cggcgagccc gcattatgcg     2220
gatcagaacg cgccgtggag cgattgcgcg atggtgccga tgctgtatag ctgggatcgt     2280
atcgcggcgg aagcggtgac cagccaggaa ctggtgccgg cgtaa                     2325
```

<210> SEQ ID NO 7
<211> LENGTH: 229
<212> TYPE: PRT

```
<213> ORGANISM: Artificial Sequence
<220> FEATURE:
<223> OTHER INFORMATION: alpha-subunit of mutatnt CPC acylase S12
      protein

<400> SEQUENCE: 7
```

| | | | | | | | | | | | | | | | |
|---|---|---|---|---|---|---|---|---|---|---|---|---|---|---|---|
| Thr | Met | Ala | Ala | Lys | Thr | Asp | Arg | Glu | Ala | Leu | Gln | Ala | Ala | Leu | Pro |
| 1 | | | | 5 | | | | | 10 | | | | | 15 | |
| Pro | Leu | Ser | Gly | Ser | Leu | Ser | Ile | Pro | Gly | Leu | Ser | Ala | Pro | Val | Arg |
| | | | 20 | | | | | 25 | | | | | 30 | | |
| Val | Gln | Arg | Asp | Gly | Trp | Gly | Ile | Pro | His | Ile | Lys | Ala | Ser | Gly | Glu |
| | | 35 | | | | | 40 | | | | | 45 | | | |
| Ala | Asp | Ala | Tyr | Arg | Ala | Leu | Gly | Phe | Val | His | Ala | Gln | Asp | Arg | Leu |
| 50 | | | | | 55 | | | | | 60 | | | | | |
| Phe | Gln | Met | Glu | Leu | Thr | Arg | Arg | Lys | Ala | Leu | Gly | Arg | Ala | Ala | Glu |
| 65 | | | | | 70 | | | | | 75 | | | | | 80 |
| Trp | Leu | Gly | Ala | Glu | Ala | Ala | Glu | Ala | Asp | Ile | Leu | Val | Arg | Arg | Leu |
| | | | | 85 | | | | | 90 | | | | | 95 | |
| Gly | Met | Glu | Lys | Val | Cys | Arg | Arg | Asp | Phe | Glu | Ala | Leu | Gly | Ala | Glu |
| | | | 100 | | | | | 105 | | | | | 110 | | |
| Ala | Lys | Asp | Met | Leu | Arg | Ala | Tyr | Ala | Ala | Gly | Val | Asn | Ala | Phe | Leu |
| | | 115 | | | | | 120 | | | | | 125 | | | |
| Ala | Ser | Gly | Ala | Pro | Leu | Pro | Ile | Glu | Tyr | Ser | Leu | Leu | Gly | Ala | Glu |
| | 130 | | | | | 135 | | | | | 140 | | | | |
| Pro | Glu | Pro | Trp | Glu | Pro | Trp | His | Ser | Ile | Ala | Val | Met | Arg | Arg | Leu |
| 145 | | | | | 150 | | | | | 155 | | | | | 160 |
| Gly | Leu | Leu | Met | Gly | Ser | Val | Trp | Phe | Lys | Leu | Trp | Arg | Met | Leu | Ala |
| | | | | 165 | | | | | 170 | | | | | 175 | |
| Leu | Pro | Val | Val | Gly | Ala | Ala | Asn | Ala | Leu | Lys | Leu | Arg | Tyr | Asp | Asp |
| | | | 180 | | | | | 185 | | | | | 190 | | |
| Gly | Gly | Gln | Asp | Leu | Leu | Cys | Ile | Pro | Pro | Gly | Val | Glu | Ala | Glu | Arg |
| | | 195 | | | | | 200 | | | | | 205 | | | |
| Leu | Glu | Ala | Asp | Leu | Ala | Ala | Leu | Arg | Pro | Ala | Val | Asp | Ala | Leu | Leu |
| | 210 | | | | | 215 | | | | | 220 | | | | |
| Lys | Ala | Met | Gly | Gly |
| 225 | | | | |

```
<210> SEQ ID NO 8
<211> LENGTH: 535
<212> TYPE: PRT
<213> ORGANISM: Artificial Sequence
<220> FEATURE:
<223> OTHER INFORMATION: beta-subunit of mutatnt CPC acylase S12 protein

<400> SEQUENCE: 8
```

| | | | | | | | | | | | | | | | |
|---|---|---|---|---|---|---|---|---|---|---|---|---|---|---|---|
| Ser | Asn | Asn | Trp | Ala | Val | Ala | Pro | Gly | Arg | Thr | Ala | Thr | Gly | Arg | Pro |
| 1 | | | | 5 | | | | | 10 | | | | | 15 | |
| Ile | Leu | Ala | Gly | Asp | Pro | His | Arg | Val | Phe | Glu | Ile | Pro | Gly | Met | Tyr |
| | | | 20 | | | | | 25 | | | | | 30 | | |
| Ala | Gln | His | His | Leu | Ala | Cys | Asp | Arg | Phe | Asp | Met | Ile | Gly | Leu | Thr |
| | | 35 | | | | | 40 | | | | | 45 | | | |
| Val | Pro | Gly | Val | Pro | Gly | Phe | Pro | His | Asn | Ala | His | Asn | Gly | Lys | Val |
| 50 | | | | | 55 | | | | | 60 | | | | | |
| Ala | Tyr | Cys | Val | Thr | His | Ala | Phe | Met | Asp | Thr | His | Asp | Leu | Tyr | Leu |
| 65 | | | | | 70 | | | | | 75 | | | | | 80 |
| Glu | Gln | Phe | Ala | Glu | Asp | Gly | Arg | Thr | Ala | Arg | Phe | Gly | Asn | Glu | Phe |
| | | | | 85 | | | | | 90 | | | | | 95 | |

```
Glu Pro Val Ala Trp Arg Arg Asp Arg Ile Ala Val Arg Gly Gly Ala
            100                 105                 110

Asp Arg Glu Phe Asp Ile Val Glu Thr Arg His Gly Pro Val Ile Ala
            115                 120                 125

Gly Asp Pro Leu Glu Gly Ala Ala Leu Thr Leu Arg Ser Val Gln Phe
            130                 135                 140

Ala Glu Thr Asp Leu Ser Phe Asp Cys Leu Thr Arg Met Pro Gly Ala
145                 150                 155                 160

Ser Thr Val Ala Gln Leu Tyr Asp Ala Thr Arg Gly Trp Gly Leu Val
                165                 170                 175

Asp His Asn Leu Val Ala Gly Asp Val Ala Gly Ser Ile Gly His Leu
            180                 185                 190

Val Arg Ala Arg Val Pro Ser Arg Pro Arg Glu Asn Gly Trp Leu Pro
            195                 200                 205

Val Pro Gly Trp Ser Gly Glu His Glu Trp Arg Gly Trp Ile Pro His
            210                 215                 220

Glu Ala Met Pro Arg Val Ile Asp Pro Gly Gly Leu Ile Val Thr
225                 230                 235                 240

Ala Asn Asn Arg Val Val Ala Asp Asp His Pro Asp Tyr Leu Cys Thr
                245                 250                 255

Asp Cys His Pro Pro Tyr Arg Ala Glu Arg Ile Met Glu Arg Leu Val
            260                 265                 270

Ala Ser Pro Ala Phe Ala Val Asp Asp Ala Ala Ile His Ala Asp
            275                 280                 285

Thr Leu Ser Pro His Val Gly Leu Leu Arg Ala Arg Leu Glu Ala Leu
            290                 295                 300

Gly Ile Gln Gly Ser Leu Pro Ala Glu Glu Leu Arg Gln Thr Leu Ile
305                 310                 315                 320

Ala Trp Asp Gly Arg Met Asp Ala Gly Ser Gln Ala Ala Ser Ala Tyr
                325                 330                 335

Asn Ala Phe Arg Arg Ala Leu Thr Arg Leu Val Thr Ala Arg Ser Gly
            340                 345                 350

Leu Glu Gln Ala Ile Ala His Pro Phe Ala Ala Val Pro Pro Gly Val
            355                 360                 365

Ser Pro Gln Gly Gln Val Trp Trp Ala Val Pro Thr Leu Leu Arg Asn
            370                 375                 380

Asp Asp Ala Gly Met Leu Lys Gly Trp Ser Trp Asp Glu Ala Leu Ser
385                 390                 395                 400

Glu Ala Leu Ser Val Ala Thr Gln Asn Leu Thr Gly Arg Gly Trp Gly
                405                 410                 415

Glu Glu His Arg Pro Arg Phe Thr His Pro Leu Ser Ala Gln Phe Pro
            420                 425                 430

Ala Trp Ala Ala Leu Leu Asn Pro Val Ser Arg Pro Ile Gly Gly Asp
            435                 440                 445

Gly Asp Thr Val Leu Ala Asn Gly Leu Val Pro Ser Ala Gly Pro Glu
            450                 455                 460

Ala Thr Tyr Gly Ala Leu Cys Arg Tyr Val Phe Asp Val Gly Asn Trp
465                 470                 475                 480

Asp Asn Ser Arg Trp Val Val Phe His Gly Ala Ser Gly His Pro Ala
                485                 490                 495

Ser Pro His Tyr Ala Asp Gln Asn Ala Pro Trp Ser Asp Cys Ala Met
            500                 505                 510
```

```
Val Pro Met Leu Tyr Ser Trp Asp Arg Ile Ala Ala Glu Ala Val Thr
        515                 520                 525

Ser Gln Glu Leu Val Pro Ala
    530                 535
```

<210> SEQ ID NO 9
<211> LENGTH: 21
<212> TYPE: DNA
<213> ORGANISM: Artificial Sequence
<220> FEATURE:
<223> OTHER INFORMATION: Universal primer for amplification of CPC
      acylase gene by PCR

<400> SEQUENCE: 9
aattaaccct cactaaaggg a                                         21

<210> SEQ ID NO 10
<211> LENGTH: 20
<212> TYPE: DNA
<213> ORGANISM: Artificial Sequence
<220> FEATURE:
<223> OTHER INFORMATION: Universal primer for amplification of CPC
      acylase gene by PCR

<400> SEQUENCE: 10
taatacgact cactataggg                                           20

<210> SEQ ID NO 11
<211> LENGTH: 19
<212> TYPE: DNA
<213> ORGANISM: Artificial Sequence
<220> FEATURE:
<223> OTHER INFORMATION: Universal primer for amplification of CPC
      acylase gene by PCR

<400> SEQUENCE: 11
ggaaacagct atgaccatg                                            19

<210> SEQ ID NO 12
<211> LENGTH: 17
<212> TYPE: DNA
<213> ORGANISM: Artificial Sequence
<220> FEATURE:
<223> OTHER INFORMATION: Universal primer for amplification of CPC
      acylase gene by PCR

<400> SEQUENCE: 12
gtaaaacgac ggccagt                                              17

<210> SEQ ID NO 13
<211> LENGTH: 58
<212> TYPE: DNA
<213> ORGANISM: Artificial Sequence
<220> FEATURE:
<223> OTHER INFORMATION: Primer for amplification of synthesized acyII
      gene by PCR

<400> SEQUENCE: 13
ataccgctcg aggtcctaga aaaaaccaag gaggtaataa ataatgacca tggcggcg       58

<210> SEQ ID NO 14
<211> LENGTH: 37
<212> TYPE: DNA
<213> ORGANISM: Artificial Sequence
<220> FEATURE:
<223> OTHER INFORMATION: Primer for amplification of synthesized
      acyII gene by PCR -continued

<400> SEQUENCE: 14
ctagctctag agatcctcat tacgccggca ccagttc　　　　　　　　　　　　　　37

<210> SEQ ID NO 15
<211> LENGTH: 46
<212> TYPE: DNA
<213> ORGANISM: Artificial Sequence
<220> FEATURE:
<223> OTHER INFORMATION: Primer for preparation of alpha-subunit
      gene by PCR

<400> SEQUENCE: 15 ttattaccttc cttgaattca ctagtcatta gccgcccatc gctttc　　　　　　　　46

<210> SEQ ID NO 16
<211> LENGTH: 46
<212> TYPE: DNA
<213> ORGANISM: Artificial Sequence
<220> FEATURE:
<223> OTHER INFORMATION: Primer for preparation of beta-subunit gene
      by PCR

<400> SEQUENCE: 16
ctagtgaatt caaggaggta ataaataatg agcaacaact gggcgg　　　　　　　　46

<210> SEQ ID NO 17
<211> LENGTH: 34
<212> TYPE: DNA
<213> ORGANISM: Artificial Sequence
<220> FEATURE:
<223> OTHER INFORMATION: Primer for amplification of beta-subunit
      fragment by PCR

<400> SEQUENCE: 17
gcgtgcgcgt ctggaagctt tgggcatcca gggc　　　　　　　　　　　　　　34

<210> SEQ ID NO 18
<211> LENGTH: 34
<212> TYPE: DNA
<213> ORGANISM: Artificial Sequence
<220> FEATURE:
<223> OTHER INFORMATION: Primer for amplification of beta-subunit
      fragment by PCR

<400> SEQUENCE: 18
gccctggatg cccaaagctt ccagacgcgc acgc　　　　　　　　　　　　　　34

<210> SEQ ID NO 19
<211> LENGTH: 65
<212> TYPE: DNA
<213> ORGANISM: Artificial Sequence
<220> FEATURE:
<223> OTHER INFORMATION: Primer for site-directed mutagenesis by PCR

<400> SEQUENCE: 19
gtcaggccga tcatatcaaa acgatcgcac gccagatgat gctgcgcata aaggcccggg　　60 atttc　　　　　　　　　　　　　　　　　　　　　　　　　　　　　　　65

<210> SEQ ID NO 20
<211> LENGTH: 65
<212> TYPE: DNA
<213> ORGANISM: Artificial Sequence
<220> FEATURE:
<223> OTHER INFORMATION: Primer for site-directed mutagenesis by PCR

```
<400> SEQUENCE: 20
gttttgatat gatcggcctg accgtgccgg gcgtgccggg ctttccgcat atggcgcata    60
acggc                                                                65

<210> SEQ ID NO 21
<211> LENGTH: 65
<212> TYPE: DNA
<213> ORGANISM: Artificial Sequence
<220> FEATURE:
<223> OTHER INFORMATION: Primer for site-directed mutagenesis by PCR

<400> SEQUENCE: 21
gttttgatat gatcggcctg accgtgccgg gcgtgccggg ctttccgcat tgcgcgcata    60
acggc                                                                65

<210> SEQ ID NO 22
<211> LENGTH: 65
<212> TYPE: DNA
<213> ORGANISM: Artificial Sequence
<220> FEATURE:
<223> OTHER INFORMATION: Primer for site-directed mutagenesis by PCR

<400> SEQUENCE: 22
gttttgatat gatcggcctg accgtgccgg gcgtgccggg ctttccgcat gcggcgcata    60
acggc                                                                65

<210> SEQ ID NO 23
<211> LENGTH: 65
<212> TYPE: DNA
<213> ORGANISM: Artificial Sequence
<220> FEATURE:
<223> OTHER INFORMATION: Primer for site-directed mutagenesis by PCR

<400> SEQUENCE: 23
gttttgatat gatcggcctg accgtgccgg gcgtgccggg ctttccgcat gtggcgcata    60
acggc                                                                65

<210> SEQ ID NO 24
<211> LENGTH: 65
<212> TYPE: DNA
<213> ORGANISM: Artificial Sequence
<220> FEATURE:
<223> OTHER INFORMATION: Primer for site-directed mutagenesis by PCR

<400> SEQUENCE: 24
gttttgatat gatcggcctg accgtgccgg gcgtgccggg ctttccgcat ctggcgcata    60
acggc                                                                65

<210> SEQ ID NO 25
<211> LENGTH: 65
<212> TYPE: DNA
<213> ORGANISM: Artificial Sequence
<220> FEATURE:
<223> OTHER INFORMATION: Primer for site-directed mutagenesis by PCR

<400> SEQUENCE: 25
gttttgatat gatcggcctg accgtgccgg gcgtgccggg ctttccgcat aatgcgcata    60
acggc                                                                65

<210> SEQ ID NO 26
<211> LENGTH: 35
```

```
<212> TYPE: DNA
<213> ORGANISM: Artificial Sequence
<220> FEATURE:
<223> OTHER INFORMATION: Primer for site-directed mutagenesis by PCR

<400> SEQUENCE: 26
ggcgtattgc gtgaccagcg cgtttatgga tatcc                                    35

<210> SEQ ID NO 27
<211> LENGTH: 35
<212> TYPE: DNA
<213> ORGANISM: Artificial Sequence
<220> FEATURE:
<223> OTHER INFORMATION: Primer for site-directed mutagenesis by PCR

<400> SEQUENCE: 27
ggatatccat aaacgcgctg gtcacgcaat acgcc                                    35

<210> SEQ ID NO 28
<211> LENGTH: 35
<212> TYPE: DNA
<213> ORGANISM: Artificial Sequence
<220> FEATURE:
<223> OTHER INFORMATION: Primer for site-directed mutagenesis by PCR

<400> SEQUENCE: 28
ggcgtattgc gtgaccctgg cgtttatgga tatcc                                    35

<210> SEQ ID NO 29
<211> LENGTH: 35
<212> TYPE: DNA
<213> ORGANISM: Artificial Sequence
<220> FEATURE:
<223> OTHER INFORMATION: Primer for site-directed mutagenesis by PCR

<400> SEQUENCE: 29
ggatatccat aaacgccagg gtcacgcaat acgcc                                    35

<210> SEQ ID NO 30
<211> LENGTH: 34
<212> TYPE: DNA
<213> ORGANISM: Artificial Sequence
<220> FEATURE:
<223> OTHER INFORMATION: Primer for site-directed mutagenesis by PCR

<400> SEQUENCE: 30
gatgggcagc gtgtggtata aactgtggcg tatg                                     34

<210> SEQ ID NO 31
<211> LENGTH: 34
<212> TYPE: DNA
<213> ORGANISM: Artificial Sequence
<220> FEATURE:
<223> OTHER INFORMATION: Primer for site-directed mutagenesis by PCR

<400> SEQUENCE: 31
catacgccac agtttatacc acacgctgcc catc                                     34

<210> SEQ ID NO 32
<211> LENGTH: 33
<212> TYPE: DNA
<213> ORGANISM: Artificial Sequence
<220> FEATURE:
<223> OTHER INFORMATION: Primer for site-directed mutagenesis by PCR

<400> SEQUENCE: 32
```
cgtggctggg gcctggttga tcataacctg gtg                                    33

<210> SEQ ID NO 33
<211> LENGTH: 33
<212> TYPE: DNA
<213> ORGANISM: Artificial Sequence
<220> FEATURE:
<223> OTHER INFORMATION: Primer for site-directed mutagenesis by PCR

<400> SEQUENCE: 33
caccaggtta tgatcaacca ggccccagcc acg                                    33

<210> SEQ ID NO 34
<211> LENGTH: 35
<212> TYPE: DNA
<213> ORGANISM: Artificial Sequence
<220> FEATURE:
<223> OTHER INFORMATION: Primer for site-directed mutagenesis by PCR

<400> SEQUENCE: 34
ggcgtattgc gtgacccatg cgtttatgga tatcc                                  35

<210> SEQ ID NO 35
<211> LENGTH: 35
<212> TYPE: DNA
<213> ORGANISM: Artificial Sequence
<220> FEATURE:
<223> OTHER INFORMATION: Primer for site-directed mutagenesis by PCR

<400> SEQUENCE: 35
ggatatccat aaacgcatgg gtcacgcaat acgcc                                  35

<210> SEQ ID NO 36
<211> LENGTH: 36
<212> TYPE: DNA
<213> ORGANISM: Artificial Sequence
<220> FEATURE:
<223> OTHER INFORMATION: Primer for site-directed mutagenesis by PCR

<400> SEQUENCE: 36
cgctgccgat cgaatatagc ctgctgggcg cggaac                                 36

<210> SEQ ID NO 37
<211> LENGTH: 36
<212> TYPE: DNA
<213> ORGANISM: Artificial Sequence
<220> FEATURE:
<223> OTHER INFORMATION: Primer for site-directed mutagenesis by PCR

<400> SEQUENCE: 37
gttccgcgcc cagcaggcta tattcgatcg gcagcg                                 36

<210> SEQ ID NO 38
<211> LENGTH: 49
<212> TYPE: DNA
<213> ORGANISM: Artificial Sequence
<220> FEATURE:
<223> OTHER INFORMATION: Primer for amplification of alpha-subunit
      containing spacerpeptide by PCR

<400> SEQUENCE: 38
gctgccgccg cccgccgcat cgctcgcatc gccgcccatc gctttcagc                   49

<210> SEQ ID NO 39
<211> LENGTH: 47
<212> TYPE: DNA

<213> ORGANISM: Artificial Sequence
<220> FEATURE:
<223> OTHER INFORMATION: Primer for amplification of beta-subunit
    containing spacerpeptide by PCR

<400> SEQUENCE: 39
gcgatgcgag cgatgcggcg ggcggcggca gcaacaactg ggcggtg                47

<210> SEQ ID NO 40
<211> LENGTH: 69
<212> TYPE: DNA
<213> ORGANISM: Artificial Sequence
<220> FEATURE:
<223> OTHER INFORMATION: Primer for amplification of CPC acylase gene
    by PCR

<400> SEQUENCE: 40
tcccctctag aaataatttt gtttaacttt aagaaggaga tatacatatg accatggcgg    60
cgaaaactg                                                            69

<210> SEQ ID NO 41
<211> LENGTH: 33
<212> TYPE: DNA
<213> ORGANISM: Artificial Sequence
<220> FEATURE:
<223> OTHER INFORMATION: Primer for amplification of CPC acylase gene
    by PCR

<400> SEQUENCE: 41
gtggtgctcg agtcattacg ccggcaccag ttc                                33

<210> SEQ ID NO 42
<211> LENGTH: 65
<212> TYPE: DNA
<213> ORGANISM: Artificial Sequence
<220> FEATURE:
<223> OTHER INFORMATION: Primer for site-directed mutagenesis by PCR

<400> SEQUENCE: 42
gtcaggccga tcatatcaaa acgatcgcac gccagatgat gctgcgcata catgcccggg    60
atttc                                                                65

<210> SEQ ID NO 43
<211> LENGTH: 50
<212> TYPE: DNA
<213> ORGANISM: Artificial Sequence
<220> FEATURE:
<223> OTHER INFORMATION: Primer for site-directed mutagenesis by PCR

<400> SEQUENCE: 43
cgtgacccat gcgtttatgg atacccatga tctgtatctg aacagtttg                50

<210> SEQ ID NO 44
<211> LENGTH: 50
<212> TYPE: DNA
<213> ORGANISM: Artificial Sequence
<220> FEATURE:
<223> OTHER INFORMATION: Primer for site-directed mutagenesis by PCR

<400> SEQUENCE: 44
caaactgttc cagatacaga tcatgggtat ccataaacgc atgggtcacg                50

<210> SEQ ID NO 45
<211> LENGTH: 34
<212> TYPE: DNA

-continued

```
<213> ORGANISM: Artificial Sequence
<220> FEATURE:
<223> OTHER INFORMATION: Primer for site-directed mutagenesis by PCR

<400> SEQUENCE: 45
gatgggcagc gtgtggttta aactgtggcg tatg                                 34

<210> SEQ ID NO 46
<211> LENGTH: 34
<212> TYPE: DNA
<213> ORGANISM: Artificial Sequence
<220> FEATURE:
<223> OTHER INFORMATION: Primer for site-directed mutagenesis by PCR

<400> SEQUENCE: 46
catacgccac agtttaaacc acacgctgcc catc                                 34
```

CEPHALOSPORIN C ACYLASE MUTANT AND METHOD FOR PREPARING 7-ACA USING SAME

This application is a national stage application of copending PCT International Application No. PCT/KR2004/002005, filed Aug. 10, 2004. This application also claims the benefit of the filing date of Korean patent application No. 10-2003-0055259, filed Aug. 11, 2003.

FIELD OF THE INVENTION

The present invention relates to a cephalosporin C(CPC) acylase mutant polypeptide derived from *Pseudomonas* sp. SE83; a gene encoding said polypeptide; an expression vector containing said gene; a microorganism transformed with said expression vector; a method for preparing said CPC acylase mutant; and a method for preparing 7-ACA using said CPC acylase mutant.

BACKGROUND OF THE INVENTION

Cephalosporin C (hereinafter, referred to as "CPC") is one of β-lactam family antibiotics produced by filamentous fungi such as *Acremonium chrysogenum*. CPC shows antibiotic activity against Gram-negative bacteria by hindering cell wall synthesis, but it is not active enough against the growth of Gram-negative bacteria. Accordingly, CPC has been mainly used for preparing intermediates for the production of semi-synthetic cephalosporin antibiotics. In particular, 7-aminoacephalosporanic acid (hereinafter, referred to as "7-ACA") prepared by removing the D-α-aminoadipoyl side chain from CPC has been used for the production of most semi-synthetic cephalosporin antibiotics that account over 40% share of the world antibiotics market.

There are two known methods for preparing 7-ACA from CPC, chemical and enzymatic methods. The chemical method of synthesizing 7-ACA from CPC uses silyl protecting groups for both amine and carboxyl groups and gives a yield of over 90%. However, this method is complicated, uneconomical and environmentally unfavorable. Therefore, the chemical method has been replaced by an enzymatic method for preparing 7-ACA which is regarded as an environmentally acceptable method.

A two-step enzymatic method widely used commercially at present comprises the two steps of converting CPC into glutaryl-7-aminocephalosporanic acid (hereinafter, referred to as "GL-7-ACA") by D-amino acid oxidase (hereinafter, referred to as "DAO") (the first step) and GL-7-ACA into 7-ACA by GL-7-ACA acylase (the second step) (see FIG. 1). However, this method gives a lower yield of 7-ACA than the chemical method, due to a large quantity of by-products generated by the reaction of hydrogen peroxide produced in the first step with the DAO substrate or the reaction product. Therefore, there has been a need to develop an efficient one-step enzymatic method for directly converting CPC into 7-ACA using a modified CPC acylase which is capable of breaking an amide linkage at the $7^{th}$ position of CPC and removing the aminoadipoyl side chain.

CPC acylase (also called together with CPC amidase or CPC amidohydrolase) active toward CPC has been found in several microorganisms, such as *Pseudomonas* sp., *Bacillus megaterium*, *Aeromonas* sp., *Arthrobacter viscous* etc., and some CPC acylase genes have been cloned and sequenced: *Pseudomonas* sp. SE83 derived acyII gene (Matsuda et al., *J. Bacteriol.* 169: 5821-5829, 1987); *Pseudomonas* sp. N176 derived CPC acylase gene (U.S. Pat. No. 5,192,678); *Pseudomonas* sp. V22 derived CPC acylase gene (Aramori et al., *J. Ferment. Bioeng.* 72: 232-243, 1991); *Pseudomonas vesicularis* B965 derived CPC amidohydrolase gene (U.S. Pat. No. 6,297,032); *Bacillus megaterium* derived CPC amidase gene (U.S. Pat. No. 5,229,274); and *Pseudomonas* sp. 130 derived CPC acylase gene (Li et al., *Eur. J. Biochem.* 262: 713-719, 1999). However, these CPC acylases are not hydrolytically active enough to cleave the amide linkage at the $7^{th}$ position of CPC, and thus, it is not suitable for a one-step enzymatic process for preparing 7-ACA from CPC.

Several genetic engineering studies have been attempted to increase the enzyme activity of CPC acylase toward CPC. For example, Fujisawa Pharmaceutical Co. (Japan) developed a CPC acylase mutant derived from *Pseudomonas* sp. N176 which shows about 2.5-fold higher specific activity toward CPC than that of a wild-type (U.S. Pat. No. 5,804,429; U.S. Pat. No. 5,336,613, Japanese Patent Publication No. 1995-222587; Japanese Patent Publication No. 1996-098686; and Japanese Patent Publication No. 1996-205864). However, such a mutant still has insufficient specific activity toward CPC to directly produce 7-ACA from CPC and exhibits end-product inhibition by 7-ACA. Therefore, it can't be used practically in the direct conversion of CPC to 7-ACA.

For the purpose of developing a CPC acylase mutant applicable to a one-step enzymatic method for preparing 7-ACA, the tertiary structure of GL-7-ACA acylase has been investigated by the present inventors, who have identified for the first time the tertiary structures of apoenzyme (Kim, et al., *Structure* 8: 1059-1068, 2000) and CAD-GL-7-ACA complex (Kim, et al., *Chem. Biol.* 8: 1253-1264, 2001; Kim, et al., *J. Biol. Chem.* 276: 48376-48381, 2001) associated with GL-7-ACA acylase derived from *Pseudomonas* sp. KAC-1 (Kim, et al., *Biotech. Lett.* 23: 1067-1071, 2001; hereinafter, referred to as "CAD") (see FIG. 2). The structures of the two CAD binary complexes suggest that the most extensive interactions between the GL-7-ACA acylase and a substrate took place in the glutaryl moiety of GL-7-ACA. Therefore, it is suggested that the hydrophilic and hydrophobic interactions between the side-chain of substrate and its binding pocket are the dominating factors in recognizing the substrate in GL-7-ACA acylase. When the chemical structures of CPC having extremely lower substrate-binding affinity and GL-7-ACA are compared, their β-lactam structures are the same, but there are some differences in the side chain (see FIG. 3). Namely, unlike the side chain of GL-7-ACA which is composed of glutaric acid, that of CPC is a D-α-aminoadipic acid. Therefore, the modeling of the structure of CAD-CPC complex suggests that the glutaric acid side chain of GL-7-ACA and the binding-related key residues of CAD are sterically crowded with respect to the carboxyl and D-form amino groups at the terminal end of D-α-aminoadipic acid side chain (see FIG. 4). Thus, if an enough space for accommodating the CPC side chain (that contains a carbon backbone greater than that of the GL-7-ACA side chain and the D-amino group) can be secured in the substrate binding site of CAD, it is considered that the specific activity of GL-7-ACA for CPC can be increased. Accordingly, the structural analysis about the "enzyme-substrate" complex of CAD may provide important information for developing a CPC acylase mutant having an increased specific activity to CPC by introducing the mutations at the active site of GL-7-ACA acylase derived from *Pseudomonas* sp. that show relatively low substrate-binding affinity.

The present inventors have therefore endeavored to develop a CPC acylase mutant having improved reactivity to CPC which can be used in a one-step enzymatic method for preparing 7-ACA from CPC.

SUMMARY OF THE INVENTION

Accordingly, it is an object of the present invention to provide a CPC acylase mutant having improved reactivity to CPC which can be advantageously used in converting CPC into 7-ACA and a functionally equivalent derivative thereof.

Another object of the present invention is to provide a nucleotide sequence encoding said CPC acylase mutant and a functionally equivalent derivative thereof.

A further object of the present invention is to provide an expression vector comprising said nucleotide sequence and a microorganism transformed with said nucleotide sequence or said expression vector.

A further object of the present invention is to provide a method for preparing a CPC acylase mutant using said transformed microorganism.

A further object of the present invention is to provide a method for preparing 7-ACA or a salt thereof from CPC using said CPC acylase mutant, a composition containing said CPC acylase mutant or the processed CPC acylase mutant.

In accordance with one aspect of the present invention, there is provided a CPC acylase mutant or a functionally equivalent derivative thereof, characterized in that at least one of the amino acids selected from the group consisting of Val121α, Gly139α and Phe169α of CPC acylase α-subunit of SEQ ID NO: 4 and Met31β, Phe58β, His70β, Ile75β, Ile176β and Ser471β of CPC acylase β-subunit of SEQ ID NO: 5 is replaced by another amino acid.

Among the CPC acylase mutants of the present invention, preferred are those, wherein:

Val121α is replaced by alanine;
Gly139α is replaced by serine;
Phe169α is replaced by tyrosine;
Met31β is replaced by leucine;
Phe58β is replaced by alanine, methionine, leucine, valine, cysteine or asparagine;
His70β is replaced by serine or leucine;
Ile75β is replaced by threonine;
Ile176β is replaced by valine; or
Ser471β is replaced by cysteine.

BRIEF DESCRIPTION OF THE DRAWINGS

The above and other objects and features of the present invention will become apparent from the following description of the invention, when taken in conjunction with the accompanying drawings which respectively show.

11a: SDS-PAGE (M: size marker; 1: cell-free extract; 2: the purified enzyme)

11b: non-denaturing PAGE (M: size marker; 1: the purified enzyme)

11c: MALDI-TOF mass spectrophotometry

Figure 12:
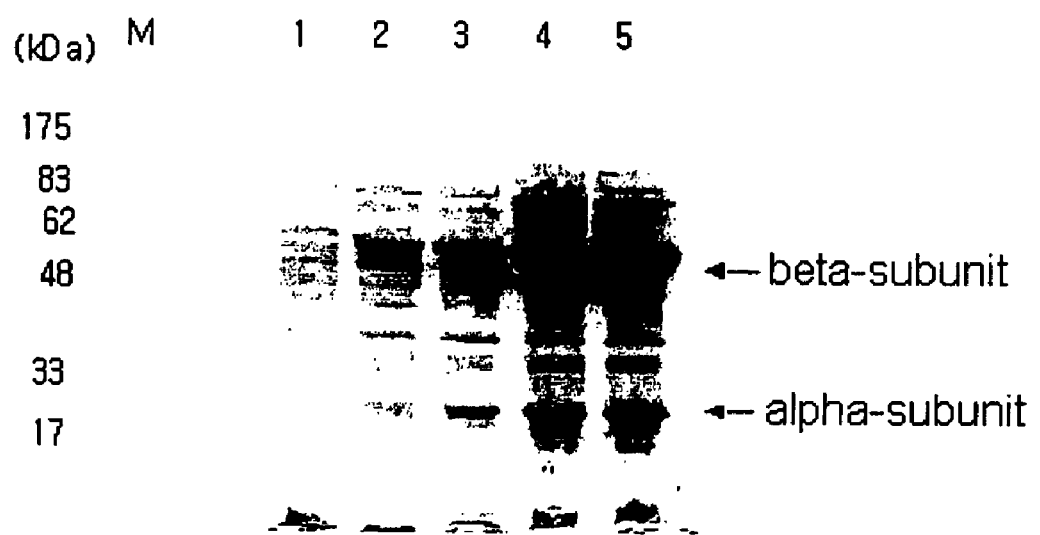
Figure 13:
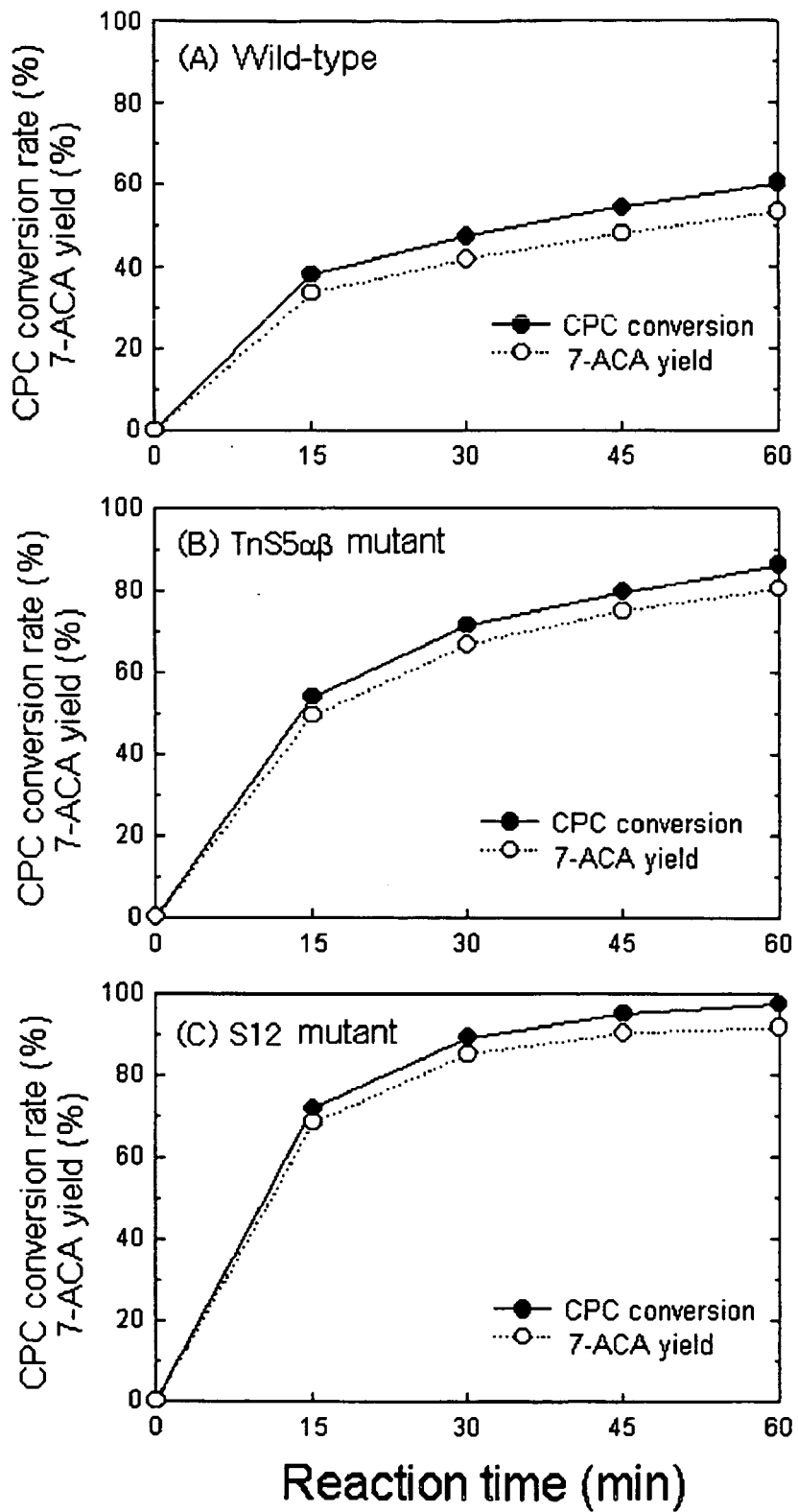
Figure 14:
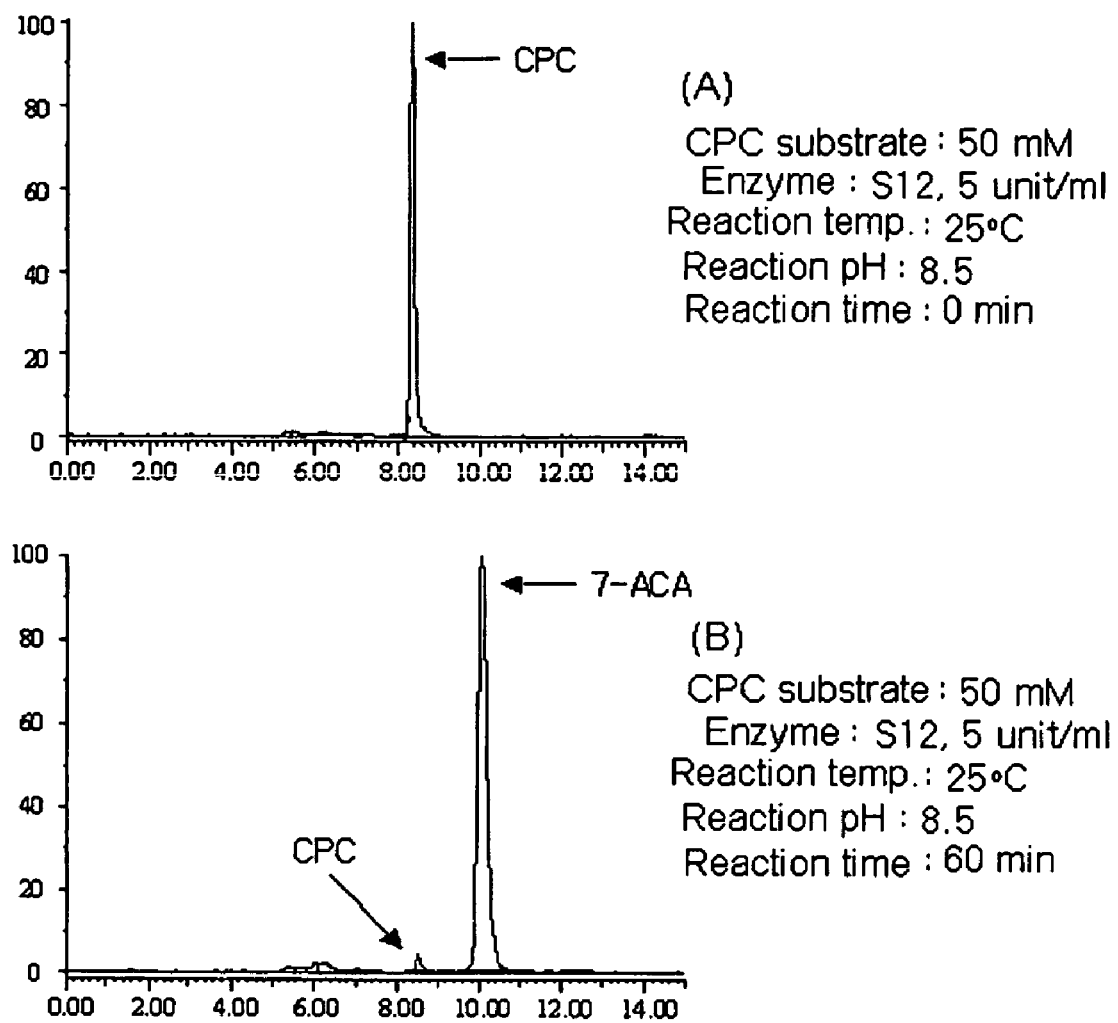

FIG. 12: the results of gel electrophoresis and Comassie blue staining of a crude enzyme isolated from *E. coli* BL21 (DE3) culture solution comprising pET29-TnS5 plasmid;

M: standard size marker, 1: 0% lactose, 48 hr cultivation
2: 0.02% lactose, 48 hr cultivation, 3: 0.2% lactose, 48 hr cultivation
4: 2% lactose, 48 hr cultivation, 5: 2% lactose, 72 hr cultivation FIG. 13: comparison of the conversion rates of CPC into 7-ACA observed for the wild-type CPC acylase, TnS5 and S12 CPC acylase mutants;

FIG. 14: the HPLC analysis result for determining 7-ACA produced from CPC by the action of the inventive S12 CPC acylase mutant.

DETAILED DESCRIPTION OF THE INVENTION

As used therein, the term "increase in the reactivity toward CPC" means increased specific activity toward CPC and/or decreased end-product inhibition by 7-ACA.

The term "functionally equivalent derivative" as used herein means a CPC acylase derivative retaining the same functional property as the inventive CPC acylase mutant. Namely, the functionally equivalent derivative includes all possible variants such as a native, synthetic or recombinant polypeptide which may be modified, i.e., by sequence mutation, deletion, insertion, substitution, inversion of single or several nucleotides and a combination thereof, capable of functioning as a CPC acylase mutant.

The term "processed CPC acylase mutant" as used herein means a CPC acylase mutant in an immobilized state not but in a free state. A CPC acylase mutant may be immobilized to a conventional carrier generally employed in the art by a conventional method such as a covalent bond, ionic bond, hydrophilic bond, physical bond, microencapsulation and so on. Further, a processed CPC acylase mutant can be prepared by a whole cell immobilization method that immobilizes a microorganism producing the CPC acylase mutant as is without further purification.

The term "GL-7-ACA acylase" as used herein generally means an enzyme which is capable of converting GL-7-ACA into 7-ACA. The term "CPC acylase" as used herein means an enzyme having specific activity toward CPC among GL-7-ACA acylases, which directly produces 7-ACA from CPC by cleaving the amide linkage at the $7^{th}$ position of CPC to remove the aminoadipoyl side chain. The term "CAD" as used herein means $Pseudomonas$ sp. KAC-1 derived GL-7-ACA acylase.

The present invention provides an amino acid sequence of a CPC acylase mutant having an improved reactivity to CPC which is derived from $Pseudomonas$ sp. SE83 and a functionally equivalent derivative thereof; a nucleotide sequence encoding said CPC acylase mutant and functionally equivalent derivative thereof.

CPC acylase gene ("acyII gene") derived from $Pseudomonas$ sp. SE83 has been used as a starting gene for developing a CPC acylase mutant in the present invention, wherein the acyII gene is newly synthesized using a DNA synthesizer based on the nucleotide sequence of CPC acylase identified by Matsuda et al. ($J.$ $Bacteriol.$ 169: 5821-5826, 1987; Gen-Bank M18278). To increase the efficiency of protein synthesis using $E.$ $coli$, the previously known amino acid sequence of AcyII is modified such that it is compatible with the codons preferred used in the $E.$ $coli$-mediated protein synthesis. For example, in the previously known amino acid sequence encoded by the acyII gene, the only codon for phenylalanine is TTC and a codon for arginine is predominantly CGC or CGG, and therefore, the amino acid sequence encoded by the acyII gene synthesized in the present invention is carried out using TTT and CGT codons for phenylalanine and arginine, respectively. The acyII gene synthesized in the present invention consists of 2,325 base pairs having the nucleotide sequence of SEQ ID NO: 1. In SEQ ID NO: 1, the open reading frame corresponding to base numbers 1 to 2,322 (2,323-2,325: termination codon) is a full-length protein encoding region and the predicted amino acid sequence derived therefrom is shown in SEQ ID NO: 2 which consists of 774 amino acids. The amino acid sequence of SEQ ID NO: 2 encoded by the acyII gene synthesized in the present invention is identical to that of the previously well-known CPC acylase, but 18% of the base pairs in the nucleotide sequence of SEQ ID NO: 1 is different from those of the existing CPC acylase gene.

The amino acid sequences deduced from most GL-7-ACA acylase (or CPC acylase) genes are composed of α-subunit, a spacer peptide, and β-subunit, in that order. The wild-type CPC acylase derived from $Pseudomonas$ sp. SE83 is generated in the form of an inactive single chain polypeptide having about 84 kDa in size after undergoing transcription and translation in a host cell. After then, twice self-digestions occur between the $230^{th}$ and the $230^{st}$ amino acids, and the $239^{th}$ and the $240^{th}$ amino acids in the amino acid sequence of SEQ ID NO: 2, which results in removing the spacer peptide consisting of 9 amino acids, and separating into a 25 kDa α-subunit and an about 58 kDa β-subunit. One of the α-subunit separated above is coupled to one of the β-subunit through hydrophobic interactions, to form an about 83 kDa dimer having acylase activity. As is generally known, the first amino acid, methionine codon needed for translation initiation during a protein synthesis in a prokaryote, is removed after the translation. Thus, an active form of the wild-type CPC acylase used in the present invention is composed of a α-subunit consisting of 229 amino acids (SEQ ID NO: 4) and a β-subunit consisting of 535 amino acids (SEQ ID NO: 5).

If a proper self-digestion does not occur in a host cell after transcription and translation of a corresponding gene, GL-7-ACA acylase (or CPC acylase) is generated in the form of an inactive polypeptide. Therefore, the self-digestion efficiency in a host cell plays an important role in obtaining an active protein. It has also been reported that the self-digestion efficiency may be lowered by several causes such as over-production of acylase in a host cell or a mutation of a specific amino acid at a spacer peptide or a mature protein, resulting in the production of an inactive protein (Li, et al., $Eur.$ $J.$ $Biochem.$ 262: 713-719, 1999; Kim, et al., $J.$ $Biol.$ $Chem.$ 276: 48376-48381, 2001). Therefore, when the improvement of the reaction property of CPC acylase is intended, the question of whether a mutation to be introduced at a specific amino acid to increase the enzyme reactivity may affect to the self-digestion efficiency must be properly addressed. Namely, since the change of self-digestion efficiency of an inactive polypeptide generated in a host cell after transcription/translation of a CPC acylase gene is directly related to the productivity of an active CPC acylase, it is difficult to select a CPC acylase mutant having an improved reactivity toward CPC without knowing the reactivity characteristics of the purified active CPC acylase mutant. To solve such problems, the present inventors have contrived a CPC acylase gene having the nucleotide sequence of SEQ ID NO: 3 based on the nucleotide sequence of SEQ ID NO: 1, which is capable of generating an active CPC acylase without the self-digestion step by individually synthesizing α- and β-subunits during the translation. The amino acid sequence encoded by the CPC acylase gene of SEQ ID NO: 3 is identical to that of SEQ ID NO: 2 encoded by CPC aclyase gene acyII, except that the nucleotide sequence encoding the spacer peptide corresponding to the $231^{st}$ to the $239^{th}$ region of SEQ ID NO: 2 is modified. Namely, a translation stop codon is inserted behind the glycine codon encoding the last amino acid of the α-subunit; and a nucleotide sequence comprising a random nucleotide sequence including a restriction enzyme site, a nucleotide sequence encoding a ribosome binding site represented as -AGGA-, another random nucleotide sequence, and a translation initiation codon (methionine), arranged in a consecutively fashion, is inserted in front of the serine codon encoding the first amino acid of β-subunit. The present inventors have contrived to form the CPC acylase gene in one operon structure by making each of the nucleotide sequences encoding the β-subunit and β-subunit to individually maintain its own structural gene. The CPC acylase gene having the nucleotide sequence of SEQ ID NO: 3 and individually expressing α-subunit and β-subunit is designated sem. Therefore, it can be expected that if the inventive CPC acylase gene sem is inserted into an appropriate expression vector and transformed to a host cell, the α-subunit and β-subunit would be individually synthesized and coupled to each other within a host cell, to obtain the dimeric form of active CPC acylase. Comparison of the characteristic features of CPC acylase purified from the $E.$ $coli$ transformant containing the sem gene of SEQ ID NO: 3 with that purified from the $E.$ $coli$ transformant containing the acyII gene of SEQ ID NO: 1 actually shows that the characteristic features of sem derived CPC acylase, e.g., molecular weight, specific activity, substrate specificity, optimal reaction temperature and pH, are identical to those of acyII derived CPC acylase. Therefore, the separate expression of the α-subunit and β-subunit may remove the cause responsible for the self-digestion efficiency of inactive polypeptide, making it easy to detect the change in the characteristic features induced by a mutation introduced at a specific amino acid residue. Thus, in the present invention the acyII gene of SEQ ID NO: 3 is employed as a starting DNA for developing a CPC acylase mutant.

The literature nomenclature of the amino acid sequence of *Pseudomonas* sp. SE83 derived CPC acylase (AcyII, SEQ ID NO: 2) employed in the present invention has adopted a consecutively numbering system starting from the methinine codon at the N-terminal end of the α-subunit as the first, to the alanine codon at the C-terminal end of the β-subunit as the last. However, since the first amino acid, methinine, and the spacer peptide are removed in a host cell after transcription and translation of a CPC aclyase gene, they do not exist in the amino acid sequence of a mature protein. Namely, the amino acid sequence of an active protein consists of the amino acid sequence of the α-subunit and the amino acid sequence of the β-subunit. Accordingly, the numbering system employed in the present invention is to consecutively number each of the α- and β-subunits existing in the active form of mature CPC acylase. Naming of a specific residue of the amino acid sequence of CPC acylase is carried out by following the conventional nomenclature as follows: the threonine, the $1^{st}$ residue of α-subunit in the amino acid sequence of SEQ ID NO: 4, is designated Thr1α; and the serine, the $1^{st}$ residue of β-subunit in the amino acid sequence of SEQ ID NO: 5, Ser1β. Accordingly, Thr1α and Ser1β mean the $2^{nd}$ residue thereonine and the $240^{th}$ residue serine in the amino acid sequence of SEQ ID NO: 2, respectively.

The naming of a specific residue introduced with a mutation among the amino acid sequence of CPC acylase is also carried out following the conventional nomenclature as follows: the mutated residue replacing the $169^{th}$ residue phenylalanine of α-subunit by a tyrosine is represented by F169αY and the mutated residue replacing the $176^{th}$ residue isoleucine of β-subunit by a valine, I176βV.

The CPC acylase mutant of the present invention has been prepared using the CPC acylase gene sem of SEQ ID NO: 3 as a starting DNA using conventional point mutation methods and genetic engineering techniques as follows (see FIG. 5).

First, in order to increase the specific activity of CPC acylase mutant to CPC, the amino acid residue to be mutated has been selected from the amino acid sequence of AcyII, based on the result of virtual mutagenesis in the tertiary structural modeling of CAD-CPC complex using a computer program. An artificial oligonucleotide including a nucleotide sequence corresponding to the mutated amino acid sequence selected above has been synthesized and subjected to PCR for inducing a site-directed mutagenesis at the CPC acylase gene. The mutated gene has been transformed into a microorganism and the transformant was cultivated under a suitable condition to produce the CPC acylase. Then, the enzyme activities of CPC acylases thus produced have been measured to select a CPC acylase mutant having an improved reactivity to CPC. The nucleotide sequence of gene encoding the selected CPC acylase mutant has been analyzed. As a result, it has been found that the mutation introduced at one or more of amino acid residues selected from the group consisting of Phe169α, Met31β, Phe58β, His70β and Ile176β in the AcyII amino acid sequence of SEQ ID NOs: 4 and 5 enhances the CPC acylase reactivity to CPC.

To further increase the reactivity of CPC acylase mutant to CPC, the selected CPC acylase mutant gene has been subjected to error-prone PCR to induce a point mutation at a random site. The mutated gene has been transformed to a host cell to construct a mutant library and the host cell containing the CPC acylase mutant having increased reactivity to CPC has been screened from the mutant library. The enzyme activities of CPC acylase mutants thus produced have been measured to select a CPC acylase mutant having an improved CPC acylase reactivity and the nucleotide sequence of the gene encoding the CPC acylase mutant selected above has been analyzed. As a result, it has been found that the mutation introduced at one or more of amino acid residues selected from the group consisting of Val121α, Gly139α, Ile75β and Ser471β in the AcyII amino acid sequence of SEQ ID NOs: 4 and 5 increases the efficiency of CPC acylase converting CPC into 7-ACA.

Therefore, the CPC acylase mutant of the present invention preferably has an amino acid sequence which is characterized in that at least one amino acid selected from the group consisting of Val121α, Gly139α and Phe169α of CPC acylase α-subunit of SEQ ID NO: 4 and Met31β, Phe58β, His70β, Ile75β, Ile176β and Ser471β of CPC acylase β-subunit of SEQ ID NO: 5 is replaced by another amino acid.

In the above amino acid substitution for increasing the CPC acylase reactivity to CPC, it is preferable to replace the specified amino acid residue with another amino acid selected from the group consisting of glycine, alanine, valine, leucine, serine, threonine, cysteine, isoleucine, methionine, proline, phenylalanine, tyrosine, tryptophan, aspartic acid, glutamic acid, asparagine, glutamine, histidine, lysine and arginine. More preferably, Val121α is replaced by alanine; Gly139α, by serine; Phe169α, by tyrosine; Met31β, by leucine; Phe58β, by asparagine, methionine, alanine, leucine, valine or cysteine; His70β, by serine or leucine; Ile75β, by threonine; Ile176β, by valnine; and Ser471β, by cysteine.

In a preferred embodiment of the present invention, a CPC acylase mutant gene designated S12 having Val121α replaced by alanine; Gly139α, by serine; Phe58', by asparagine; Ile75β, by thereonine; Ile176β, by valnine; and Ser471β, by cysteine has been prepared. The S12 mutant gene has an increased specific activity to CPC but shows decreased end-product inhibition by 7-ACA. The S12 mutant gene has the nucleotide sequence of SEQ ID NO: 6 and the active CPC acylase mutant encoded by the S12 mutant gene consists of the α-subunit of SEQ ID NO: 7 and the β-subunit of SEQ ID NO: 8.

The present invention also includes a functionally equivalent derivative of the CPC acylase mutant. A functionally equivalent derivative in the present invention means a CPC acylase derivative retaining the general feature of the inventive CPC acylase mutant. Namely, the functionally equivalent derivative includes all possible variants such as native, synthetic or recombinant polypeptides modified by sequence mutation, deletion, insertion, substitution, inversion of single or several nucleotides and a combination thereof, which are capable of functioning as a CPC acylase mutant.

Further, the present invention includes the polynucleotide encoding said CPC acylase mutant having an improved reactivity to CPC or a functionally equivalent derivative thereof. Preferably, the polynucleotide has the nucleotide sequence of SEQ ID NO: 6. The functionally equivalent derivative in the present invention means a polynucleotide and its derivative retaining the crucial functional property of the polynucleotide(s) encoding the α-subunit and/or β-subunit of the CPC acylase mutant. Therefore, the present invention includes within its scope not only the polynucleotide encoding the CPC acylase mutant which comprises the α-subunit linked to the β-subunit with a specific spacer peptide but also a polynucleotide encoding both the α- and β-subunits of the CPC acylase mutant without a spacer peptide. Furthermore, a polynucleotide encoding only the α-subunit of CPC acylase mutant and a polynucleotide encoding only the β-subunit of CPC acylase also fall within the scope of the present invention.

The present invention also includes, in its scope, a polynucleotide comprising a nucleotide sequence of the inventive CPC acylase mutant gene or a nucleotide sequence deduced from the CPC acylase mutant amino acid sequence as well as a nucleotide sequence generated through the codon degeneracy of genetic code in the nucleotide sequence of the inventive CPC acylase mutant gene.

Further, the present invention includes a recombinant expression vector comprising the inventive CPC acylase mutant encoding gene. Said recombinant expression vector may be prepared by inserting a DNA fragment containing the CPC acylase mutant gene and a suitable transcription/translation regulatory sequence into an appropriate expression vector according to a conventional method (Sambrook, et al., *Molecular Cloning*, Cold Spring Harbor Laboratory, 1989). Any expression vector capable of expressing a foreign gene in a host cell can be employed in the present invention. For example, preferable expression vectors include, but are not to limited to, a plasmid, a phage vector and an integration vector.

The recombinant expression vector prepared above may be introduced into a suitable host cell according to a conventional transformation method (Sambrook, et al., the supra). Bacteria, *actinomyces*, yeast, fungi, an animal cell, an insect cell or a plant cell can be employed as a host cell suitable for the expression of a recombinant DNA. Among these host cells, preferred are bacteria such as *E. coli* or *Bacillus* sp.; *actinomyces* such as *Streptomyces* sp.; yeast such as *Scaaharomyces* sp., *Humicola* sp. or *Pichia* sp.; fungi such as *Aspergillus* sp. or *Trichoderma* sp.; and a CPC producing microorganism such as *Cephalosporium* sp. or *Acremonium* sp.

In a preferred embodiment of the present invention, *E. coli* BL21(DE3) is transformed with the recombinant expression vector comprising the inventive CPC acylase mutant gene S12 (SEQ ID NO: 6) to obtain an *E. coli* transformant designated *E. coli* BL21(DE3)/pET-S12 which was deposited on Jul. 30, 2003 with the Korean Collection for Type Cultures (KCTC) (Address: Korea Research Institute of Bioscience and Biotechnology (KRIBB), #52, Oun-dong, Yusong-ku, Taejon, 305-333, Republic of Korea) under the accession number KCTC 10503BP, in accordance with the terms of Budapest Treaty on the International Recognition of the Deposit of Microorganism for the Purpose of Patent Procedure.

The CPC acylase mutant may be prepared by culturing said transformed microorganism introduced with the expression vector comprising the CPC acylase mutant encoding gene or functionally equivalent derivative thereof in a suitable medium under a proper condition.

Further, the CPC acylase mutant may be also prepared by culturing a microorganism transformed with the expression vector comprising only an α-subunit encoding gene of CPC acylase mutant or a functionally equivalent derivative thereof and a microorganism transformed with the expression vector comprising only a β-subunit encoding gene of CPC acylase mutant or a functionally equivalent derivative thereof in a suitable medium under a proper condition, separately producing the α-subunit protein and β-subunit protein in respective transformed microorganisms and mixing the two subunit proteins purified therefrom in vitro.

It is possible to use the CPC acylase mutant thus prepared as is or in a purified form to produce the desired product, 7-ACA, in a one-step enzymatic method. The CPC acylase mutant may be purified by a conventional protein purification method using various column chromatographic techniques based on the characteristics of the CPC acylase, with or without minor modifications in accordance with specific purposes. Further, it is also possible to purify the CPC acylase mutant by affinity chromatography, taking advantage of the binding affinity such as the binding affinity of a histidine peptide to a nickel column or the binding affinity of a cellulose-binding domain (CBD) with a cellulose.

The inventive CPC acylase mutant may be also used in an immobilized form. The immobilization of CPC acylase mutant may be conducted by a conventional method using a carrier, e.g., a natural polymer such as cellulose, starch, dextran and agarose; a synthetic polymer such as polyacrylamide, polyacrylate, polymetacrylate and Eupergit C; or a mineral such as silica, bentonite and metal. The CPC acylase mutant may be coupled to said carrier by a conventional immobilization method such as a covalent bond, ionic bond, hydrophilic bond, physical absorption or microencapsulation. In addition, it is also capable to immobilize the CPC acylase mutant by forming a covalent bond between the carrier and the enzyme via the action of glutaraldehyde or cyanogen bromide. Preferably, the microorganism cell producing the CPC acylase mutant may be immobilized as is by a whole cell immobilization method without purifying the CPC acylase mutant. In order to increase the reactivity of CPC acylase mutant produced by a microorganism, it is also possible to make a hole at the cell wall or apply a cell surface expression technique thereto.

Further, the present invention provides a method for preparing 7-ACA of formula II or a salt thereof from CPC of formula I using said CPC acylase mutant.

In the following formula, R is acetoxy (—OCOCH$_3$), hydroxy (—OH), hydrogen (—H) or a salt thereof. Preferably, R is acetoxy (—OCHCH$_3$) and a salt is an alkali metal salt such as a sodium, potassium or lithium salt.

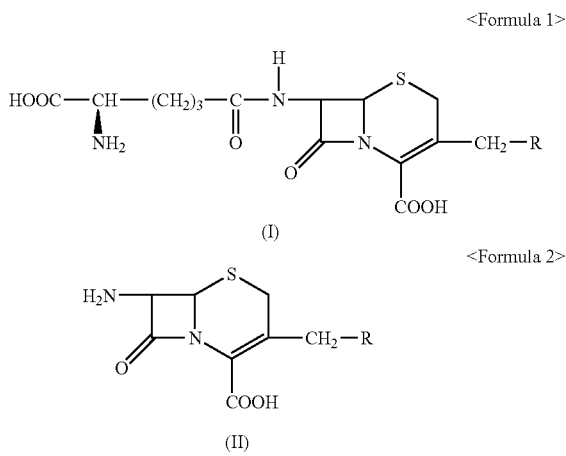

<Formula 1>

(I)

<Formula 2>

(II)

7-ACA (II) may be produced by contacting CPC (I) with the inventive CPC acylase mutant, wherein the CPC acylase may be used in the form of a culture solution of the CPC acylase mutant producing strain, or in the form of an composition comprising the CPC acylase mutant, the purified free enzyme itself or an immobilized form of the enzyme. Preferably, the contact reaction of the CPC acylase mutant with CPC (I) may be carried out in an aqueous solution. The preferable concentration of CPC (I) ranges from 1 to 500 mM; the amount of added CPC acylase mutant, from 0.1 to 100

U/ml; pH of the reaction mixture, from 7 to 10; the reaction time, from 0.1 to 24 hr; and the reaction temperature, 4 to 40° C. 7-ACA (II) prepared by above enzyme reaction can be isolated and purified from the reaction mixture by conventional methods.

Further, it is possible to produce 7-ACA (II) by contacting the inventive CPC acylase mutant with CPC (I) in vivo. In particular, 7-ACA (II) may be produced by the steps of introducing the CPC acylase mutant encoding gene or a functionally equivalent derivative thereof into a microorganism having a biosynthetic activity of CPC such as *Acremonium crysozenum*; culturing the transformant in a suitable medium under a proper condition; and spontaneously contacting the CPC acylase mutant with the CPC (I) biosynthesized in said transformant.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

EXAMPLE 1

Preparation of CPC Acylase Mutant Having an Improved Reactivity to CPC

<1-1> Preparation of CPC Acylase Mutant Based on the Structural Information

Figure 1:
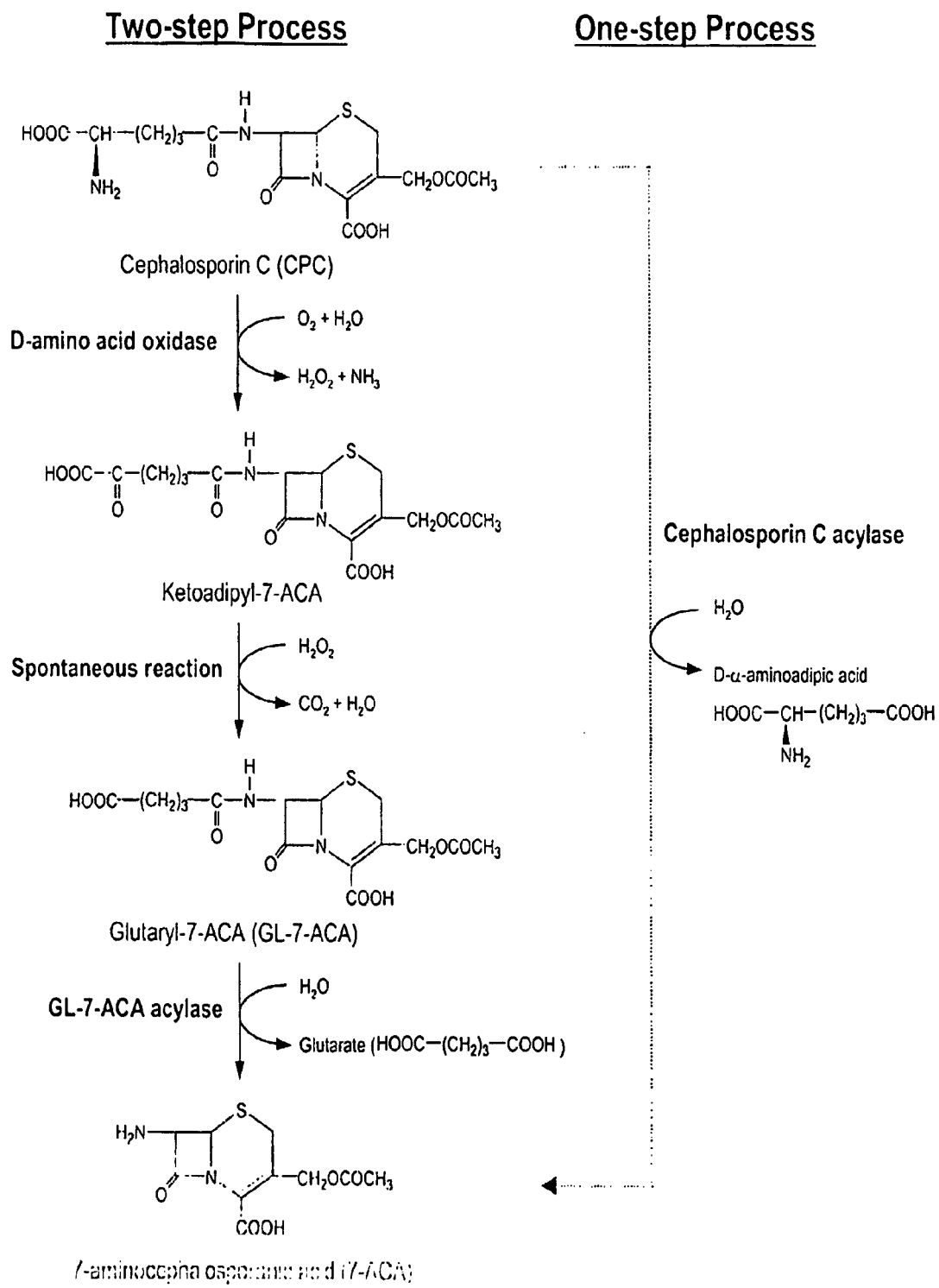
FIG. 1: schematic procedures of one-step and two-step enzymatic methods for preparing 7-ACA from CPC.
Figure 2:
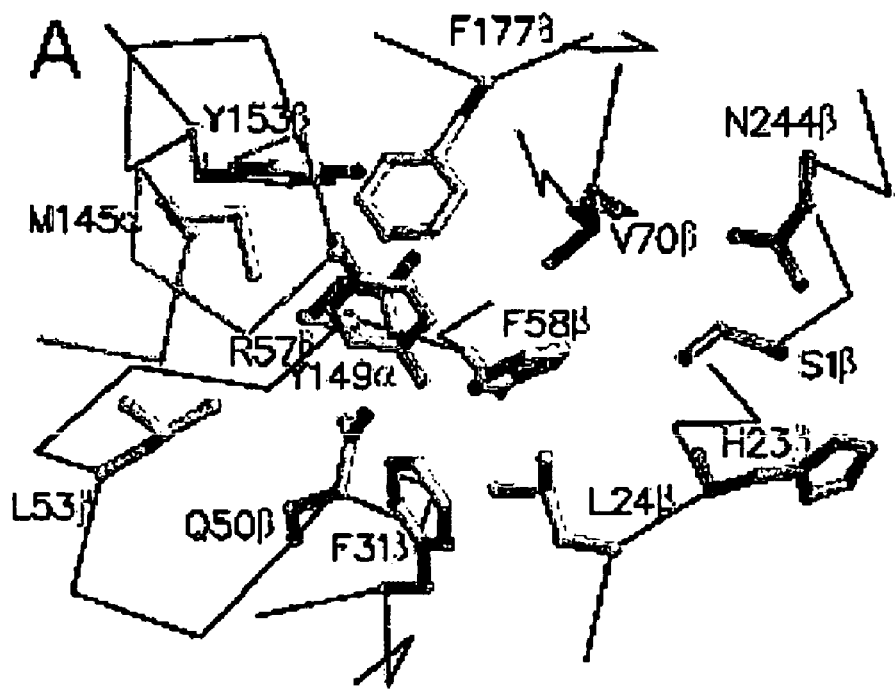
FIG. 2: the tertiary structure of *Pseudomonas* sp. KAC-1 derived CAD-GL-7-ACA complex (A) and a general scheme for the binding residues adjacent to its active site (B)
Figure 2:
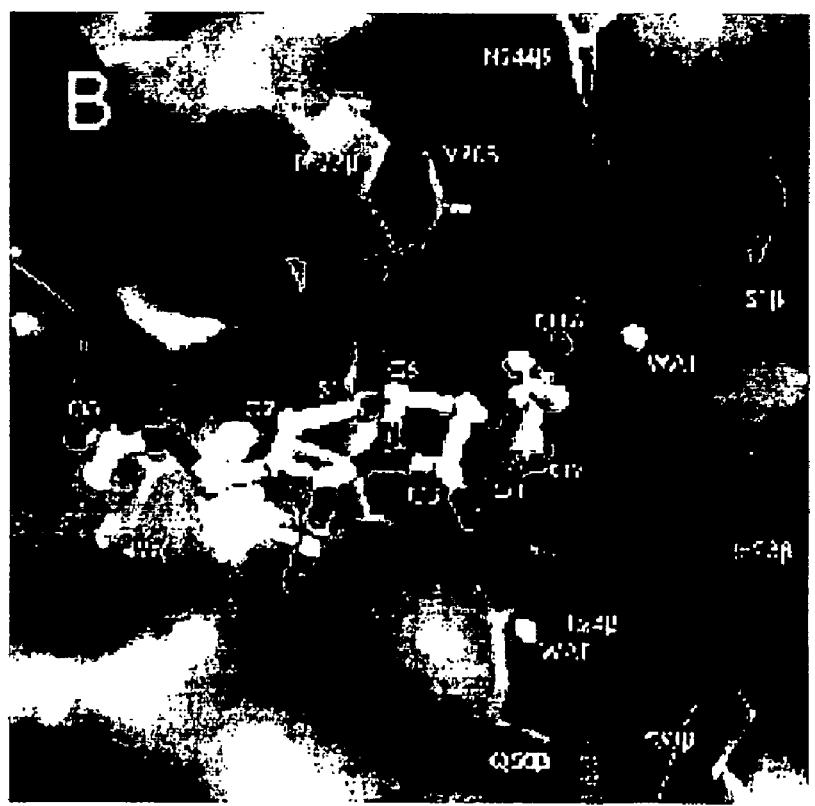
Figure 3:
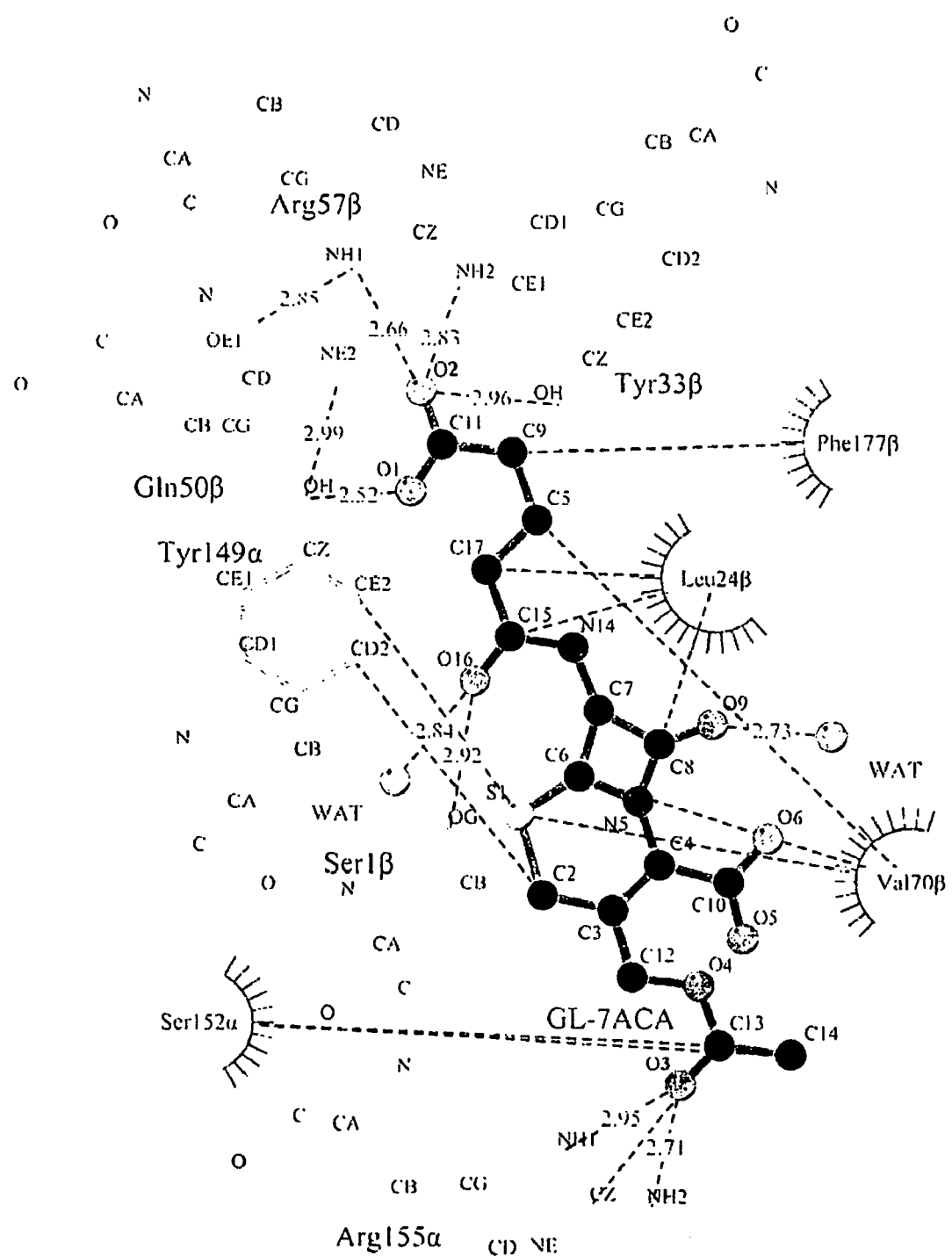
FIG. 3: the binding pattern of *Pseudomonas* sp. KAC-1 derived CAD with GL-7-ACA.

<1-1-1> Selection of AcyII Amino Acid Residue to be Mutated Based on the Structural Information The tertiary structure of CAD-GL-7-ACA complex has been determined lately (Kim, et al., *Chem. Biol.* 8:1253-1264, 2001; Kim, et al., *J. Biol. Chem.* 276: 48376-48381, 2001). As illustrated in FIG. 3, Arg57β, Tyr33β, Tyr149α and Arg155α existing in the substrate-binding site of CAD directly form hydrogen bonds with GL-7-ACA, and Phe177β, Leu24β and Val70β bind to GL-7-ACA via hydrophobic interactions. In addition, although Gln50β makes no direct interaction with GL-7-ACA, it forms hydrogen bonds with Arg570 and Tyr149α to arrange these residues at suitable positions for a catalytic reaction. Meanwhile, in the coupling of CAD and GL-7-ACA, a beta-lactam core of GL-7-ACA comprising an acetoxy group, a six-membered ring and a four-membered beta-lactam ring does not significantly affect on the binding with active site residues. If anything, a glutaric acid region as GL-7-ACA side chain has the largest effect on a substrate binding by precisely coupling with Arg57β, Tyr33β, Tyr149α and Phe177β (FIGS. 2 and 3). In addition, it has been presumed that Leu24β and Val70β play a role in stimulating a catalytic reaction of Ser1β by making a substrate occupied to a suitable position.

Figure 4:
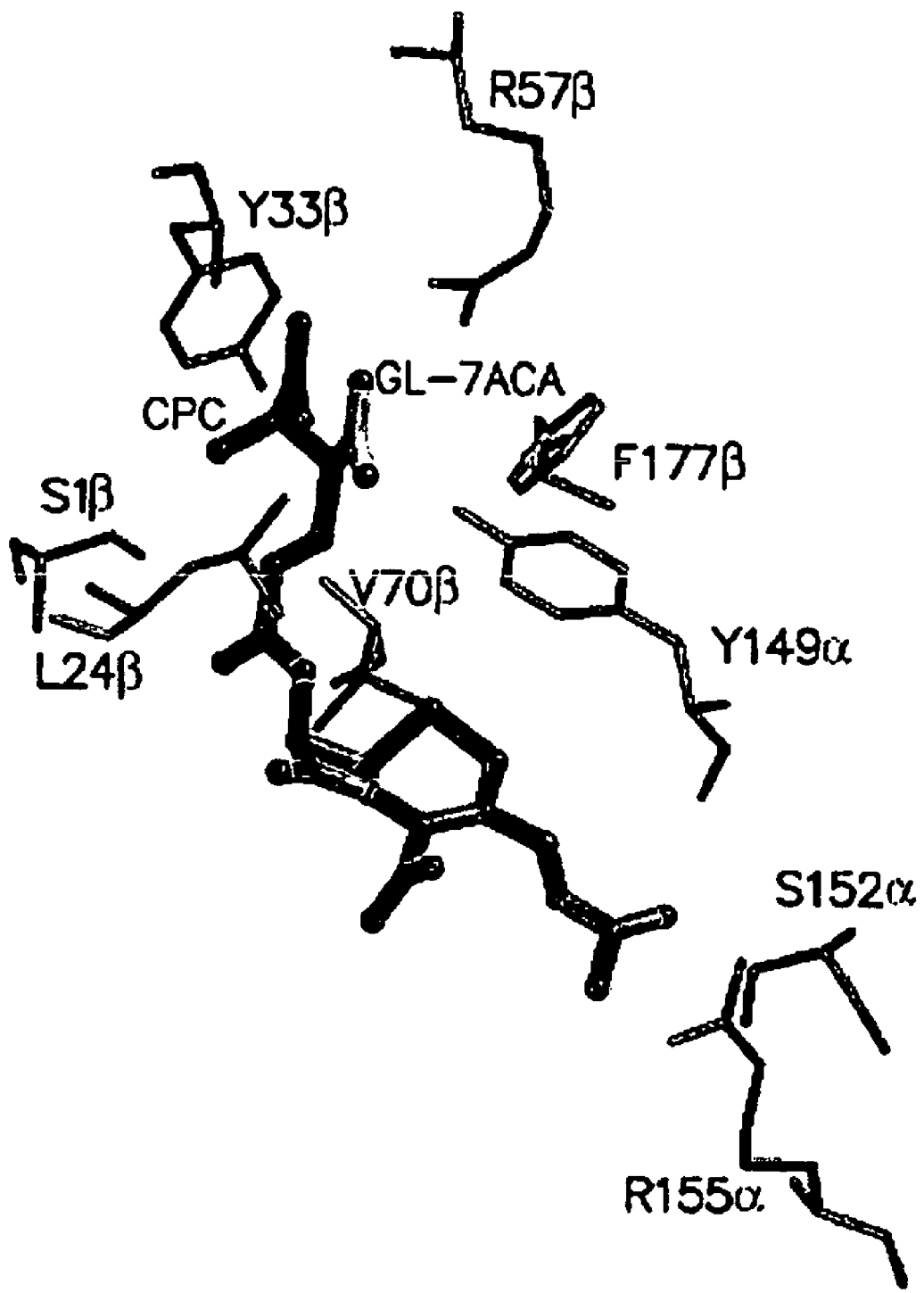
FIG. 4: modeling of *Pseudomonas* sp. KAC-1 derived CAD-CPC complex.

Meanwhile, as a result of overlapping the tertiary structure of CAD-GL-7-ACA complex with that of CAD-CPC complex, key residues of CAD such as Arg57β, Tyr33β, Phe1770 and Tyr149α involving in the coupling with a glutaric acid side chain of GL-7-ACA collide with the carboxyl group and the D-form amino group at a terminal region of D-α-aminoadipic acid side chain of CPC (FIG. 4). From these modeling results, if a space enough for accommodating the CPC side chain (namely, said a carbon backbone and a D-amino group additionally existed at the CPC side chain as compared with the GL-7-ACA side chain) within a substrate-binding site of CAD can be secured, it might be expected to increase the specific activity of GL-7-ACA acylase for CPC.

Meanwhile, it has been presumed from the result of comparing structures of CAD, penicillin G acylase and *Pseudomonas* sp. derived GL-7-ACA acylase that *Pseudomonas* sp. derived GL-7-ACA acylase shows similar substrate-binding and reaction patterns to the rest (Kim, et al., *Chem. Biol.* 8: 1253-1264, 2001; Fritz-Wolf, et al., *Protein Sci.* 11: 92-103, 2002). Further, it has been reported that while CAD has no activity to CPC, *Pseudomonas* sp. derived GL-7-ACA acylase (AcyII) shows about 5% level of acylase activity to CPC as compared with GL-7-ACA (Matsuda, et al., *J. Bacteriol.* 169: 5815-5820, 1987). Thus, there has an advantage in developing a CPC acylase mutant based on AcyII having a constant level of enzyme activity to CPC rather than based on CAD having no enzyme activity to CPC. Accordingly, the present invention has employed *Pseudomonas* sp. SE83 derived CPC acylase gene (acyII) as a fundamental gene for developing a CPC acylase mutant.

The present invention intended to prepare a CPC acylase mutant having a better specific activity for CPC than the wild-type AcyII by selecting an active site of AcyII based on the tertiary structure of CAD-CPC complex and a virtual mutagenesis information, and then, performing a site-directed mutagenesis to AcyII residues be involved in interfering with a CPC binding among the selected active site. Table 1 shows AcyII residues corresponding to active site resides of CAD subjected to site-directed mutagenesis.

TABLE 1

| CAD residue | AcyII residue |
|---|---|
| Tyr33β | Met31β |
| Phe58β | Phe58β |
| Val70β | His70β |
| Phe177β | Ile176β |
| Tyr149α | Phe169α |

Figure 5:
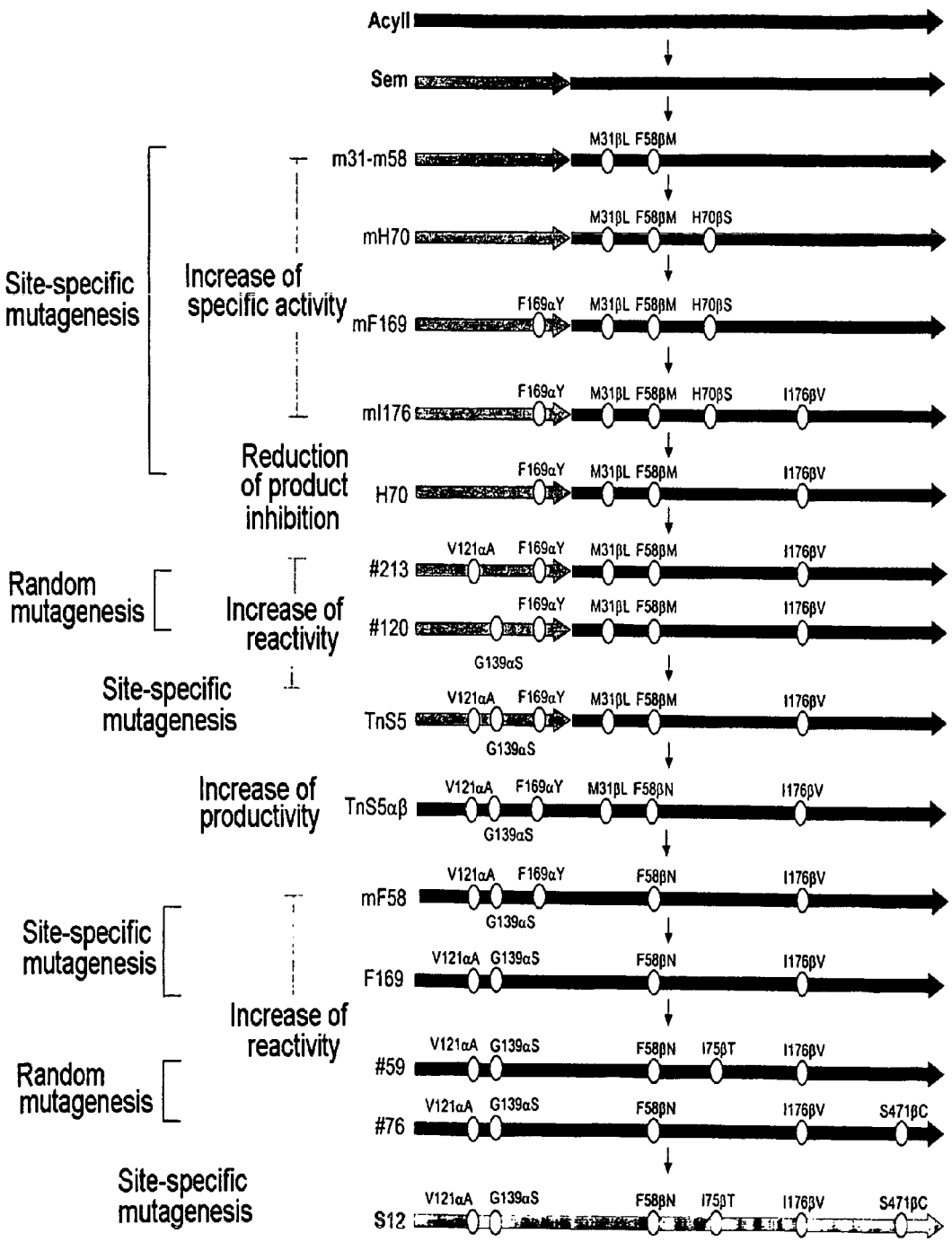
FIG. 5: a schematic representation of the procedure for preparing the inventive CPC acylase mutants.

Based on the results of the tertiary structural modeling of CAD-CPC complex, site-directed mutagenesis was conducted to Phe58β, Met31β, Ile176β and Phe169α residues of AcyII corresponding to Phe58β, Tyr33β, Phe177β and Tyr149α residues of CAD that are presumed to seriously inhibit the binding of CPC side chain, and His70β residue of AcyII corresponding to Val70β residue of CAD which stimulates to catalytic reaction of Ser1β active site (FIG. 5).

<1-1-2> Preparation of pBCPC and pBSEM plasmids pBCPC plasmid was constructed by inserting the acyII structural gene DNA fragment of SEQ ID NO: 1 into XhoI/XbaI sites of pBC KS(+) vector (Stratagene, USA) as follows. First, the acyII structural gene was synthesized by using a DNA synthesizer based on the DNA nucleotide sequence of *Pseudomonas* sp. SE83 derived CPC acylase gene (acyII) and the amino acid sequence of protein AcyII encoded thereby (GenBank Accession No. M18278). At this time, the amino acid sequence encoded by the acyII gene was identical to that published in the literatures, but its nucleotide sequence has been synthesized to be made some modifications that the acyII gene may includes one or more preferred codons in *E. coli*.

PCR was performed to introduce a recognition site of restriction enzyme and a ribosome-binding site into the acyII structural gene. PCR reaction solution (100 μl) contained 10 ng of the synthesized acyII gene DNA, 50 μmol each of CPC-F primer (SEQ ID NO: 13) and CPC-R primer (SEQ ID NO: 14), 0.2 mM dNTP mixture, Taq buffer solution (5 mM KCl, 5 mM Tris-HCl, (pH 8.3), 1.5 mM MgCl$_2$), and 2.5 unit of ExTaq polymerase (Takara, Japan). Reactions were initiated by pre-denaturation for 5 min at 95° C. in a programmable thermal cycler (Peltier Thermal Cycler PTC-200; MJ Research, USA). PCR conditions consisted of 25 cycles of 1 min at 95° C. (denaturation), 30 sec at 58° C. (annealing), and 1 min 30 sec at 72° C. (polymerization), with a final elongation of 10 min at 72° C. (post-polymerization). After the PCR amplification, about 2.5 kb of PCR product was digested with XbaI/XhoI and purified with a purification kit (QIAEX II Gel Extraction Kit; Qiagen, Germany), to obtain an insert DNA. Further, pBC KS(+) vector DNA was digested with XbaI/XhoI and subjected to dephosphorylation with CIP, to obtain a vector DNA. The insert DNA and vector DNA were subjected to ligation using T4 DNA ligase (Roche, Germany) at 16° C. for 12 to 16 hr and transformed to E. coli MC1061 strain by electrophoration. The E. coli strain was spread onto a LB agar plate containing 25 μg/ml of chloramphenicol and cultured at 30° C. incubator for overnight to select a transformant. The plasmid was purified from the selected transformant and the nucleotide sequence of insert DNA was analyzed. Out of this, pBCPC plasmid containing the acyII structural gene of SEQ ID NO: 1 was prepared and the E. coli transformant containing pBCPC plasmid was designated E. coli MC1061(pBCPC).

pBSEM plasmid was constructed by inserting the sem structural gene DNA fragment of SEQ ID NO: 3 into XhoI/XbaI sites of pBC KS(+) vector (Stratagene, USA). A series of PCR amplifications were performed as follows: pBCPC plasmid as a template and M13-R primer (SEQ ID NO: 11) and αORF-R primer (SEQ ID NO: 15) to obtain 0.8 kb of PCR product; pBCPC plasmid as a template and βORF-F primer (SEQ ID NO: 16) and HindIII-R primer (SEQ ID NO: 18) to obtain about 0.96 kb of PCR product; and pBCPC plasmid as a template and HindIII-F primer (SEQ ID NO: 17) and M13-F primer (SEQ ID NO: 12) to obtain 0.75 kb of PCR product. 0.8 kb, 0.96 kb and 0.75 kb of PCR products obtained above were mixed and subjected to PCR under the same PCR condition described above except that primers did not added, to obtain about 2.5 kb of PCR product which is ligated three PCR products in one. After then, about 2.5 kb of PCR product was subjected to PCR using T3 primer (SEQ ID NO: 9) and T7 primer (SEQ ID NO: 10) to is amplify the sem gene DNA fragment of about 2.5 kb in size. After the PCR amplification, about 2.5 kb of PCR product was digested with XbaI/XhoI and purified with a purification kit (QIAEX II Gel Extraction Kit; Qiagen, Germany), to obtain an insert DNA. Further, pBC KS(+) vector DNA was digested with XbaI/XhoI and subjected to dephosphorylation with CIP to obtain a vector DNA. The insert DNA and vector DNA were subjected to ligation using T4 DNA ligase (Roche, Germany) at 16-C for 16 hr and transformed to E. coli MC1061 strain by electrophoration. The E. coli strain was spread onto a LB agar plate containing 25 μg/ml of chloramphenicol and cultured at 30° C. incubator for overnight to select a transformant. The plasmid was purified from the selected transformant and the nucleotide sequence of insert DNA was analyzed. As a result, pBSEM plasmid containing the sem structural gene of SEQ ID NO: 3 was prepared and the E. coli transformant containing pBSEM plasmid was designated E. coli MC1061 (pB-SEM).

To compare the productivity of CPC acylase by pBCPC plasmid derived E. coli transformant with that by pBSEM plasmid derived E. coli transformant, a CPC acylase crude enzyme solution obtained from each E. coli transformant was prepared as follows. Each E. coli transformant was inoculated into 3 ml of a LB medium (1% Bacto-Tryptone, 0.5% Yeast Extract, 0.5% NaCl) containing 25 μg/ml of chloramphenicol and cultured at 30° C., 200 rpm for 16 hr with vigorous shaking. 50 μl of the culture solution was transformed to 50 ml of a new LB medium containing 25 μg/mg of chloramphenicol and further cultured at 25° C., 200 rpm for 48 hr with vigorous shaking. The culture solution was subjected to centrifugation at 4° C., 8,000 rpm for 10 min to separate a precipitate and the precipitate washed twice with 0.1 M Tris-HCl buffer solution (pH 8.0). This precipitate was suspended in 5 ml of the same buffer solution and subjected to ultra-sonication at 4° C. for 10 min. And then, the suspension was subjected to centrifugation at 4° C., 15,000 rpm for 20 min, to separate a supernatant which can be used as a CPC acylase crude enzyme solution.

The enzyme activity of CPC acylase mutant to CPC was measured according to the method described by Park et al. with minor modifications as follows (Park, et al., *Kor. J. Appl. Microbiol. Biotechnol.* 23: 559-564, 1995). A substrate solution was prepared by dissolving CPC (purity 74.2%; CJ Corp., Korea) in 0.1 M Tris-HCl buffer solution (pH 8.0) at a concentration of 20 mg/ml and adjusting pH to 8 with 1 N NaOH. 20 μl of the CPC solution was mixed with 20 μl of the crude enzyme solution prepared above and the reaction mixture was incubated at 37° C. for 5 min. After the reaction, the mixture (200 μl) of 50 mM NaOH and 20% glacial acetic acid (1:2) was added thereto to stop the reaction. 200 μl of the supernatant recovered from the reaction mixture by centrifugation was mixed with 40 μl of 0.5% (w/v) PDAB (p-dimethylaminobenzaldehyde; Sigma, USA) dissolved in a methanol and the reaction mixture was incubated at 37° C. for 10 min. After the reaction, the absorbance of reaction mixture was measured at 415 nm and quantified by comparing with a calibration curve of standard material. At this time, 1 unit has been defined as the amount of enzyme capable to produce 1 μmole of 7-ACA from CPC per minute. Meanwhile, the specific activity of CPC acylase mutant for CPC was determined by measuring the amount of protein remaining in the enzyme solution according to the method described by Bradford (Bradford, M., *Anal. Biochem.* 72: 248-254, 1976) and representing it as an active unit corresponding to 1 mg of protein. The reactivity of CPC acylase mutant to CPC was determined by the following steps of adding the same amount of protein to a reaction mixture, performing an enzyme reaction for a fixed time, measuring the amount of 7-ACA produced in the reaction mixture, and representing it as a relative value. The end-product inhibition by 7-ACA was determined by adding a protein corresponding to the same active unit to a reaction mixture, performing an enzyme reaction for a fixed time; measuring the amount of 7-ACA produced in the reaction mixture, and representing it as a relative value.

As a result of measuring the enzyme activity to CPC, while the productivity of CPC acylase produced by E. coli transformant MC1061(pBCPC) was about 97 unit/l, that by E. coli transformant MC1061 (PBSEM) was only about 11 unit/l.

<1-1-3> Preparation of Met31β/Phe58β Double Mutant

To develop a CPC acylase mutant having an improved reactivity to CPC, Met31β/Phe58β double mutant was prepared as follows. As shown in the tertiary structural modeling of CAD-CPC complex, since the CPC side chain additionally contains a carbon backbone and a D-amino group as compared with the GL-7-ACA side chain, CAD needs a large space for binding with CPC than GL-7-ACA. To secure the space enough for binding with CPC, two residues within the substrate-binding site of AcyII was subjected to a simultaneous mutation. With fixing His57β of AcyII corresponding to Arg570 of CAD as the most important residue for the binding of CPC side chain, Met31β of AcyII being regarded to collide with a carboxyl group and a D-amino group at the terminal end of CPC side chain was replaced by leucine. At the same time, to further secure the space for the binding of CPC side chain by inducing a change of torsion rotation at His57β side chain of AcyII, Phe58β of AcyII was replaced by another amino acid residue having a relatively small side chain such as alanine, valine, leucine, methionine, cysteine or asparagine. As a result, M31βL/F58βM, M31βL/F58βC, M31βL/F58βL, M31βL/F58βA, M31βL/F58βV and M31βL/F58βN double mutants were prepared by overlapping PCR (Ho, et al., Gene 15: 51-59, 1989). The procedure for preparing these double mutants was set forth in detail as follows.

PCR reaction solution (100 μl) for a site-directed mutagenesis contained 10 ng of template DNA, 50 pmol each of forward and reverse primers, 0.2 mM dNTP mixture, Taq buffer solution (5 mM KCl, 5 mM Tris-HCl, (pH 8.3), 1.5 mM MgCl$_2$), and 2.5 unit of ExTaq polymerase (Takara, Japan). Reactions were initiated by denaturation for 5 min at 95° C. in a programmable thermal cycler (Peltier Thermal Cycler PTC-200; MJ Research, USA). PCR conditions consisted of 25 cycles of 1 min at 95° C., 30 sec at 58° C., and 60 to 90 sec at 72° C., with a final elongation of 10 min at 72° C.

In particular, a series of PCR amplifications for preparing M31βL/F58βM double mutant were performed using the following template and primers: pBSEM plasmid as a template and M13-R primer (SEQ ID NO: 11) and M31βL-R primer (SEQ ID NO: 19) to obtain 1.0 kb of PCR product; and pBSEM plasmid as template and F58βM-F primer (SEQ ID NO: 20) and M13-F primer (SEQ ID NO: 12) to obtain 1.6 kb of PCR product.

1.0 kb and 1.6 kb of PCR products obtained above were mixed and subjected to PCR under the same condition except that primers did not added, to obtain about 2.5 kb of PCR product which is formed in one by connecting two PCR products with each other. After then, about 2.5 kb of PCR product was subjected to PCR using T3 primer (SEQ ID NO: 9) and T7 primer (SEQ ID NO: 10) to amplify the double mutant DNA fragment of about 2.5 kb in size. After the PCR amplification, about 2.5 kb of PCR product was digested with XbaI/XhoI and purified with a purification kit (QIAEX II Gel Extraction Kit; Qiagen, Germany), to obtain an insert DNA. Further, pBC KS(+) vector DNA was digested with XbaI/XhoI and subjected to dephosphorylation with CIP, to obtain a vector DNA. The insert DNA and vector DNA were subjected to ligation using T4 DNA ligase (Roche, Germany) at 16° C. for 16 hr and is transformed to E. coli MC1061 strain by electrophoration. The E. coli strain was spread onto a LB agar plate containing 25 μg/ml of chloramphenicol and cultured at 30° C. incubator for overnight to select a transformant containing the double mutant gene. The plasmid was purified from the selected transformant and the nucleotide sequence of insert DNA was analyzed to confirm the mutated residue.

M31βL/F58βC, M31βL/F58βL, M31βL/F58βA, M31βL/F58βV and M31βL/F58βN double mutants were prepared according to the same method described above. At this time, for M31βL/F58βC, M13-R primer (SEQ ID NO: 11) and M31βL-R primer (SEQ ID NO: 19), and F58βC-F primer (SEQ ID NO: 21) and M13-F primer (SEQ ID NO: 12) were employed for the overlapping PCR amplification; for M31βL/F58βL, M13-R primer (SEQ ID NO: 11) and M31βL-R primer (SEQ ID NO: 19), and F58βL-F primer (SEQ ID NO: 24) and M13-F primer (SEQ ID NO: 12); for M31βL/F58βA, M13-R primer (SEQ ID NO: 11) and M31βL-R primer (SEQ ID NO: 19), and F58βA-F primer (SEQ ID NO: 22) and M13-F primer (SEQ ID NO: 12); for M31βL/F58βV, M13-R primer (SEQ ID NO: 11) and M31βL-R primer (SEQ ID NO: 19), and F58βV-F primer (SEQ ID NO: 23) and M13-F primer (SEQ ID NO: 12); and for M31βL/F58βN, M13-R primer (SEQ ID NO: 11) and M31βL-R primer (SEQ ID NO: 19), and F58βN-F primer (SEQ ID NO: 25) and M13-F primer (SEQ ID NO: 12).

The specific activity of double mutants obtained above for CPC was measured by using the crude enzyme solution of each CPC acylase mutant according to the same method as described in Example <1-1-2>. As a result, it has been confirmed that the specific activity of M31βL/F58βM, M31βL/F58βC, M31βL/F58βN, M31βL/F58βL, M31βL/F58βA and M31βL/F58βV double mutants show 2.4-, 2.3-, 2.0-, 1.8-, 1.6- and 1.6-fold higher than that of the wild-type AcyII, respectively.

<1-1-4> Preparation of Met31β/Phe58β/His70β Triple Mutant

To further increase the specific activity of M31βL/F58βM showing the highest increased specific activity among 6 double mutants, His70β of AcyII corresponding to Val70β of CAD which stimulates a catalytic reaction of active site S1β was replaced by serine or leucine to prepare a triple mutant.

M31βL/F58βM/H70βS triple mutant was prepared by using a QuickChange™ site-directed mutagenesis kit (Stratagene, USA) according to the manufacturer's instruction. PCR reaction solution (50 μl) contained 40 ng of M31βL/F58βM double mutant DNA, 100 pmol each of H70βS-F primer (SEQ ID NO: 26) and H70βS-R primer (SEQ ID NO: 27), 1 μl of dNTP mixture, 5 μl of buffer solution (100 mM KCl, 100 mM (NH$_4$)$_2$SO$_4$, 200 mM Tris-HCl, (pH 8.8), 20 mM MgSO$_4$, 1% Triton X-100 and 1 mg/ml of BSA), and 2.5 unit of pfuTurbo™ DNA polymerase (Strategene, USA). Reactions were initiated by denaturation for 30 sec at 95° C. in a programmable thermal cycler (Peltier Thermal Cycler PTC-200; MJ Research, USA). PCR conditions consisted of 16 cycles of 30 sec at 95° C., 1 min at 55° C., and 12 min at 68° C. After the PCR amplification, 10 unit of DpnI restriction enzyme was added to the PCR reaction solution and incubated at 37° C. for 1 hr to remove the template DNA wherein any mutation does not occur. The mutant DNA was purified with a purification kit (QIAEX II Gel Extraction Kit; Qiagen, Germany) and transformed to E. coli MC1061 strain by electrophoration. The E. coli strain was spread onto a LB agar plate containing 25 μg/ml of chloramphenicol and cultured at 30° C. incubator for overnight to select a transformant. The plasmid was purified from the selected transformant and the nucleotide sequence of insert DNA was analyzed to confirm the mutated residue.

M31βL/F58βM/H70βL triple mutant was prepared by using a QuickChange™ site-directed mutagenesis kit (Stratagene, USA) according to the same method as described above except that H70βL-F primer (SEQ ID NO: 28) and H70βL-R primer (SEQ ID NO: 29) were employed.

The specific activity of triple mutant for CPC was measured by using the crude enzyme solution of each CPC acylase mutant according to the same method as described in Example <1-1-2>. As a result, the specific activity of M31βL/F58βM/H70βS and M31βL/F58βM/H70βL triple mutants showed 3.2- and 2.4-fold higher than that of M31βL/F58βM double mutant, respectively.

<1-1-5> Preparation of Phe169α/Met31β/Phe58β/His70β Fourfold Mutant

To further increase the specific activity of M31βL/F58βM/H70βS showing the highest increased specific activity between two triple mutants, Phe169α of AcyII corresponding to Tyr149α of CAD which helps CPC to be located at a suitable position for an efficient catalytic reaction of active site S1β was replaced by tyrosine to prepare a fourfold mutant, F169αY/M31βL/F58βM/H70βS. Since a tyrosine side chain additionally has a hydroxyl group (—OH) as compared with a phenylalanine side chain, it can stimulate a catalytic reaction of S1α P by forming a hydrogen bond with a CPC side chain and/or adjacent residues thereof.

F169αY/M31βL/F58βM/H70βS fourfold mutant was prepared by using a QuickChange™ site-directed mutagenesis kit (Stratagene, USA) according to the same method as described in Example <1-1-4> except that M31βL/F58βM/H70βS triple mutant as a template and F169αY-F primer (SEQ ID NO: 30) and F169αY-R primer (SEQ ID NO: 31) were employed.

The specific activity of F169αY/M31βL/F58βM/H70βS fourfold mutant for CPC was measured by using the crude enzyme solution of fourfold mutant according to the same method as described in Example <1-1-2>. As a result, the specific activity of F169αY/M31βL/F58βM/H70βS fourfold mutant increased 2.1-fold higher than that of M31βL/F5813M/H70βS triple mutant.

<1-1-6> Preparation of Phe169α/Met31β/Phe58β/His70β/Ile176β Fivefold Mutant

To further increase the specific activity of F169αY/M31βL/F58βM/H70βS fourfold mutant to CPC, Ile176β of AcyII corresponding to Phe177β of CAD which may be involved in interfering with the binding of a CPC side chain was replaced by valine to prepare a fivefold mutant, F169αY/M31βL/F58βM/H70βS/Ile176βV. In Example <1-1-3>, Phe58β of AcyII was replaced by methionine. Meanwhile, Ile176β of AcyII is very closely located to Phe58β of AcyII as well as supposed to interfere with the CPC binding. Thus, for the more efficient binding of CPC substrate side chain, Ile176β was replaced by valine which has a side chain having a similar structure but smaller size than isoleucine.

F169αY/M31βL/F58βM/H70βS/I176βV fivefold mutant was prepared by using a QuickChange™ site-directed mutagenesis kit (Stratagene, USA) according to the same method as described in Example <1-1-4> except that F169αY/M31βL/F58βM/H70βS fourfold mutant as a template and Ile176βV-F primer (SEQ ID NO: 32) and Ile176βV-R primer (SEQ ID NO: 33) were employed.

The specific activity of F169αY/M31βL/F58βM/H70βS/I176βV fivefold mutant for CPC was measured by using the crude enzyme solution of fivefold mutant according to the same method as described in Example <1-1-2>. As a result, the specific activity of F169αY/M31βL/F58βM/H70βS/I76βV fivefold mutant increased 2.4-fold higher than F169αY/M31βL/F58βM/H70βS fourfold mutant.

<1-2> Preparation of CPC Acylase Mutant Having an Improved Reactivity to CPC

<1-2-1> Preparation of Phe169α/Met31β/Phe58β/Ile176β Fourfold Mutant

The reason why it is difficult to apply an existing CPC acylase to a one-step enzymatic method for producing 7-ACA on a large scale is that the conversion efficiency of CPC into 7-ACA is very low due to the end-product inhibition by 7-ACA as well as the CPC acylase showing a low specific activity for CPC. Meanwhile, it can be known from a series of site-directed mutagenesis for increasing the specific activity of CPC acylase mutant in Example <1-1> that the mutation of His70β significantly increases the specific activity of CPC acylase mutant for CPC but severely increases the level of end-product inhibition by 7-ACA. Thus, F169αY/M31βL/F58βM/H70βS/I176βV fivefold mutant of Example <1-1-6> was subjected to a reverse mutagenesis of H70βS into a wild-type residue, histidine, to prepare F169αY/M31βL/F58βM/I176βV fourfold mutant (FIG. 5). F169αY/M31βL/F58βM/I176βV fourfold mutant was prepared according to the same method as described in Example <1-1-4> except that F169αY/M31βL/F58βM/H70βS/I176βV fivefold mutant as a template and H70β-F primer (SEQ ID NO: 34) and H70β-R primer (SEQ ID NO: 35) were employed.

Figure 6:
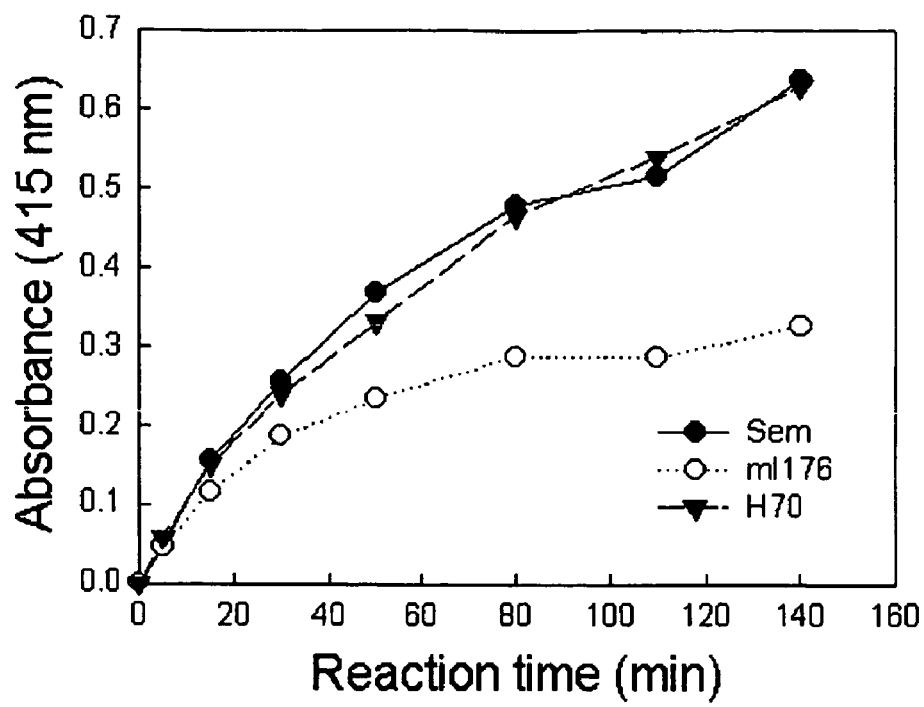
FIG. 6: comparison of the end-product inhibition by 7-ACA observed for the wild-type CPC acylase (-●-, Sem), F169αY/M31βL/F58βM/I176βV fourfold CPC acylase mutant (H70) and F169αY/M31βL/F58βM/H70βS/I176βV fivefold CPC acylase mutant (-○-, mI176)

The end-product inhibition was measured by using an enzyme solution corresponding to the same active unit after the preparation of each crude enzyme solution of wild-type, F169αY/M31βL/F58βM/H70βS/I176βV fivefold mutant and F169αY/M31βL/F58βM/I176βV fourfold mutant by the same method as described in Example <1-1-2>. As a result, it has been confirmed that the reverse mutation of H70βS in F169αY/M31βL/F58βM/H70βS/I176βV fivefold mutant into a wild-type residue, histidine decreases the end-product inhibition by 7-ACA to the similar level of wild-type enzyme (FIG. 6).

<1-2-2> Preparation of Gly139α/Phe169α/Met31β/Phe58β/Ile176β and Val121α/Phe169α/Met31β/Phe58β/Ile176β Fivefold Mutants To further increase the reactivity of F169αY/M31βL/F58βM/I176βV fourfold mutant to CPC, the fourfold mutant DNA was subjected to error-prone PCR to construct a mutant library having a point mutation at a random site. At this time, an error rate in said error-prone PCR was adjusted to be occurred a substitution at one amino acid residue for one fourfold mutant gene on the average. The particular procedure of constructing a mutant library was as follows.

PCR reaction solution (100 μl) for error-prone PCR contained 5 ng of F169αY/M31βL/F58βM/I176βV fourfold mutant DNA, 50 pmol each of T3 primer (SEQ ID NO: 9) and T7 primer (SEQ ID NO: 10), 0.2 mM each of dATP and dGTP, 1.0 mM each of dCTP and dTTP, 5 mM KCl, 5 mM Tris-HCl, (pH 8.3), 3.5 mM MgCl$_2$, 0.025 mM MnCl$_2$ and 5 unit of rTaq DNA polymerase (Takara, Japan). Reactions were initiated by denaturation for 3 min at 95° C. in a programmable thermal cycler (Peltier Thermal Cycler PTC-200; MJ Research, USA). PCR conditions consisted of 20 cycles of 1 min at 95° C., 30 sec at 58° C., and 90 sec at 72° C., with a final elongation of 10 min at 72° C. After the error-prone PCR amplification, about 2.5 kb of PCR product was digested with XbaI/XhoI and purified with a purification kit (QIAEX II Gel Extraction Kit; Qiagen, Germany), to obtain an insert DNA. Further, pBSEM plasmid DNA was digested with XbaI/XhoI to obtain 3.4 kb of DNA fragment used as a vector DNA. The insert DNA and vector DNA were subjected to ligation using T4 DNA ligase (Roche, Germany) at 16° C. for 16 hr and transformed to E. coli MC1061 strain by electrophoration. The E. coli strain was spread onto a LB agar plate containing 25 μg/ml of chloramphenicol and cultured at 30° C. incubator for overnight to construct a mutant library.

The CPC acylase mutant having an improved reactivity to CPC was screened from the mutant library obtained above as follows.

E. coli MC1061 transformant containing the CPC acylase mutant gene introduced a point mutation at a random site by error-prone PCR was inoculated in a 96-well plate filling 200 μl of LB medium containing 25 μg/ml of chloramphenicol and cultivated at 30° C., 180 rpm for 60 to 70 hr with vigorous shaking. 100 μl of each culture solution taken from the well plate was transferred to a new 96-well plate. 100 μl of a cell lysis solution (0.1 M Tris-Cl buffer solution (pH 8.0) containing 2 mg/ml lysozyme, 4 mM EDTA, 0.4% Triton X-100) was added thereto and leaved at 30° C. for 2 hr. After then, 50 μl of the mixture of 2.5% (w/v) CPC solution dissolved in 0.1 M Tris-Cl buffer solution (pH 8.0) and 5 mM 7-ACA was added to each well and the well plate was kept at 28° C. for 14 to 16 hr to induce a hydrolysis reaction of CPC. At this time, the reason why 7-ACA was added to the CPC solution is for facilitating the screening of CPC acylase mutant showing an improved specific activity for CPC and/or the decreased end-product inhibition by 7-ACA. After the hydrolysis reaction of CPC, the reaction mixture was subjected to centrifugation at 4,200 rpm for 20 min to separate a supernatant and 50 μl of the supernatant was transferred to a new 96-well plate. After 160 μl of a stop solution (acetic acid:250 mM NaOH, 2:1) was added to each well to stop the enzyme reaction, 40 μl of a developing agent (0.5% (w/v) PDAB solution dissolved in a methanol) was added thereto and the well plate leaved at room temperature for 10 min. The well plate was then loaded on a microplate reader to measure an absorbance at 415 nm and the CPC acylase mutant having an improved specific activity for CPC was selected by comparing the measured absorbance value.

As a result of randomly screening about 25,000 colonies from said random mutant library, 2 mutants (#120 and #213) showing the higher absorbance value than that of F169αY/M31βL/F58βM/I176βV fourfold mutant used as a template for a random mutagenesis were selected. It has been confirmed by a sequence analysis that #120 mutant has the substitution of Gly139α by serine (G139αS/F169αY/M31βL/F58βM/I176βV fivefold mutant) and #213 mutant, the substitution of Val 121α by alanine (V121αA/F169αY/M31βL/F58βM/I176βV fivefold mutant) (FIG. 5).

Figure 7:
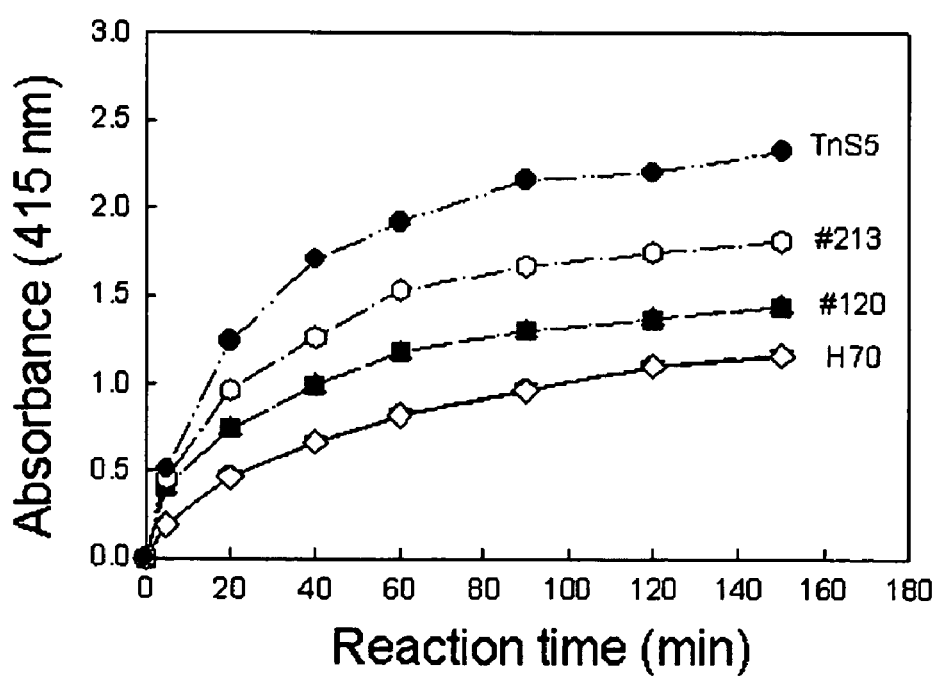
FIG. 7: comparison of the reactivities toward CPC of F169αY/M31βL/F58βM/I176βV fourfold CPC acylase mutant (-◇-, H70), V121αA/F169αY/M31βL/F58βM/I176βV fivefold CPC acylase mutant (-○-, #213), G139αS/F169αY/M31βL/F58βM/I176βV fivefold CPC acylase mutant (-■-, #120) and V121αA/G139αS/F169αY/M31βL/F58βM/I176βV sixfold CPC acylase mutant (-●-, TnS5)

Further, the reactivity of #120 and #213 mutants to CPC were measured by using the crude enzyme solution of each mutant according to the same method as described in Example <1-1-2>. As a result, it has been confirmed that #120 and #213 mutants show the further increased reactivity to CPC than F169αY/M31βL/F58βM/I176βV fourfold mutant of Example <1-2-1> (FIG. 7).

<1-2-3> Preparation of Val121α/Gly139α/Phe169α/Met31β/Phe58β/Ile176β Sixfold Mutant It has been confirmed from the results of Example <1-2-2> that the incorporation of V121αA or G139αS mutation into F169αY/M31βL/F58βM/I176βV fourfold mutant increases the reactivity of CPC acylase mutant to CPC. Thus, in order to further increase the reactivity to CPC, V121αA/G139αS/F169αY/M31βL/F58βM/I176βV sixfold mutant was prepared by incorporating G139αS mutation of #120 mutant into #213 mutant (FIG. 5). The inventive sixfold mutant was prepared according to the same method as described in Example <1-1-4> except that #213 mutant DNA as a template and G139αS-F primer (SEQ ID NO: 36) and G139αS-R primer (SEQ ID NO: 37) were employed for PCR. The present invention has designated the CPC acylase mutant gene encoding V121αA/G139αS/F169αY/M31βL/F58M/I176βV sixfold mutant as TnS5.

The reactivity of V121αA/G139αS/F169αY/M31βL/F58βM/I176βV sixfold mutant to CPC was measured by using the crude enzyme solution of sixfold mutant according to the same method as described in Example <1-1-2>. As a result, it has been confirmed that the reactivity of V121αA/G139αS/F169αY/M31βL/F58βM/I176βV sixfold mutant (TnS5) to CPC increases rather than those of #213 and #120 mutants (FIG. 7).

<1-3> Preparation of pBC-TnS5αβ Plasmid

The TnS5 gene encoding V121αA/G139αS/F169αY/M31βL/F58βM/I176βV sixfold mutant is the CPC acylase mutant gene which is designed to express α-subunit and β-subunit separately in a host cell and generate the active form of CPC acylase via a spontaneous contact of these two subunits such as the sem gene.

To induce the formation of active CPC acylase mutant from the TnS5 gene which consists of each one of α- and β-subunits obtained through a self-digestion process after the transcription and translation of CPC acylase mutant gene in a host cell such as the wild-type acylase gene (acyII), the present invention prepared a TnS5αβ gene encoding the sixfold CPC acylase mutant wherein the spacer peptide of wild-type CPC acylase (AcyII) was inserted into between α-subunit and β-subunit of V121αA/G139αS/F169αY/M31βL/F58βM/I176βV sixfold mutant (FIG. 5). The method for preparing the TnS5αβ gene was in detail as follows.

The TnS5 gene was inserted into XhoI/XbaI sites of pBC-KS(+) vector to prepare pBC-TnS5 plasmid. Twice PCR amplifications were performed by using pBC-TnS5 plasmid as a template and M13-R primer (SEQ ID NO: 11) and αCPC-R primer (SEQ ID NO: 38) to obtain 0.8 kb of PCR product and pBC-TnS5 plasmid as a template and PCPC-F primer (SEQ ID NO: 39) and M13-F primer (SEQ ID NO: 12) to obtain 1.7 kb of PCR product. 0.8 kb and 1.7 kb of PCR products obtained above were mixed and subjected to PCR under the same condition except that primers did not added, to obtain about 2.5 kb of PCR product which is formed in one by connecting two PCR products with each other. After then, 2.5 kb of PCR product was subjected to PCR using T3 primer (SEQ ID NO: 9) and T7 primer (SEQ ID NO: 10) to amplify the DNA fragment containing the TnS5αβ gene. After the PCR amplification, about 2.5 kb of PCR product was digested with XbaI/XhoI and purified with a purification kit (QIAEX II Gel Extraction Kit; Qiagen, Germany), to obtain an insert DNA. Further, pBC KS(+) vector DNA was digested with XbaI/XhoI and subjected to dephosphorylation with CIP, to obtain a vector DNA. The insert DNA and vector DNA were subjected to ligation using T4 DNA ligase (Roche, Germany) at 16° C. for 16 hr and transformed to E. coli MC1061 strain by electrophoration. The E. coli strain was spread onto a LB agar plate containing 25 μg/ml of chloramphenicol and cultured at 30° C. incubator for overnight to select a transformant. The plasmid was purified from the selected transformant and the nucleotide sequence of insert DNA was analyzed. Out of this, pBC-TnS5αβ plasmid containing the TnS5αβ gene was prepared.

In order to examine the productivity of CPC acylase mutant by the TnS5αβ gene, each of TnS5 and TnS5αβ genes encoding V121αA/G139αS/F169αY/M31βL/F58βM/I176βV sixfold mutant was inserted at pBC-KS(+) vector to prepare pBC-TnS5 and pBC-TnS5αβ recombinant plasmids, respectively, and each recombinant plasmid was transformed to E. coli MC1061 to obtain E. coli transformant MC1061(pBC-TnS5) and MC1061 (pBC-TnS5αβ). Each E. coli transformant was cultivated in 50 ml of a LB broth containing 25 μg/ml of chloramphenicol at 25° C., 200 rpm for 48 hr with vigorous shaking and the enzyme activity to CPC was measured by using the crude enzyme solution prepared from the transformant culture solution according to the same method as described in Example <1-1-2>. As a result, the productivity of CPC acylase produced by each E. coli transformant MC1061(pBC-TnS5) and MC1061(pBC-TnS5αβ) was about 78 unit/E and 162 unit/l, respectively. From these results, it has been confirmed that the sixfold CPC acylase mutant formed by a self-digestion process after the transcription and translation of CPC acylase mutant gene in a host cell such as TnS5αβ shows about 2-fold higher productivity than the sixfold CPC acylase mutant formed by a spontaneous contact of α-subunit and β-subunit expressed separately in a host cell such as TnS5.

Further, the crude enzyme solution prepared from the culture solution of *E. coli* transformant MC1061(pBC-TnS5αβ) was subjected to a denaturing polyacrylamide gel electrophoresis (12% SDS-PAGE) to examine the expression pattern of protein. As a result, there was no inactive precursor band of about 83 kDa in size, which means that most of the inactive precursor form convert into the active form of CPC acylase mutant by an efficient self-digestion after the transcription and translation of TnS5αβ gene under the culture condition of the present invention (FIG. 7). Therefore, the TnS5αβ gene has been employed as a template DNA for developing a CPC acylase mutant in the following.

<1-4> Preparation of CPC Acylase Mutant Having a Additionally Increased Reactivity to CPC <1-4-1> Preparation of Val121α/Gly139α/Phe169α/Phe58β/Ile176β Fivefold Mutant The present invention prepared the CPC acylase mutant genes TnS5 and TnS5αβ encoding V121αA/G139αS/F169αY/M31βL/F58βM/I176βV sixfold mutant having an improved reactivity to CPC by a series of site-directed mutagenesis and a random mutagenesis in Examples <1-1> to <1-3>. In these mutagenesis procedures for preparing the TnS5αβ sixfold mutant, Met31β being supposed to collide with a carboxyl group and a D-amino group at the terminal end of CPC side chain was replaced by leucine and Phe58β was replaced by methionine, cysteine or asparagine at the same time to secure the space enough for the efficient binding of CPC side chain by changing a torsion rotation at His 57β side chain. Thus, the present invention optimized Met31β and Phe58β residues in V121αA/G139αS/F169αY/M31βL/F58βM/I176βV sixfold mutant to further increase the reactivity to CPC as follows.

The present invention performed a reverse mutagenesis of M31βL into a wild-type residue, methionine and a substitution of F58βM by asparagine or cysteine using the TnS5αβ sixfold mutant DNA as a template to prepare 4 mutants (V121αA/G139αS/F169αY/F58βN/I176βV, V121αA/G139αS/F169αY/F58βC/I76βV, V121αA/G139αS/F169αY/M31βL/F58βN/I176βV, V121αA/G139αS/F169αY/M31βL/F58βC/I176βV). These mutants were prepared according to the same method for preparing M31βL/F58βM double mutant as described in Example <1-1-3>. At this time, the overlapping PCR was performed using the following primers: for V121αA/G139αS/F169αY/M31βL/F58βC/I176βV, M13-R primer (SEQ ID NO: 11) and M31βL-R primer (SEQ ID NO: 19), and F58βC-F primer (SEQ ID NO: 21) and M13-F primer (SEQ ID NO: 12); for V121αA/G139αS/F169αY/M31βL/F58βN/I176βV, M13-R primer (SEQ ID NO: 11) and M31βL-R primer (SEQ ID NO: 19), F58βN-F primer (SEQ ID NO: 25) and M13-F primer (SEQ ID NO: 12); for V121αA/G139αS/F169αY/F58βC/I176βV, M13-R primer (SEQ ID NO: 11) and M31β-R primer (SEQ ID NO: 42), and F58βC-F primer (SEQ ID NO: 21) and M13-F primer (SEQ ID NO: 12); for V121αA/G139αS/F169αY/F58βN/I176βV, M13-R primer (SEQ ID NO: 11) and M31β-R primer (SEQ ID NO: 42), and F58βN-F primer (SEQ ID NO: 25) and M13-F primer (SEQ ID NO: 12).

Figure 8:
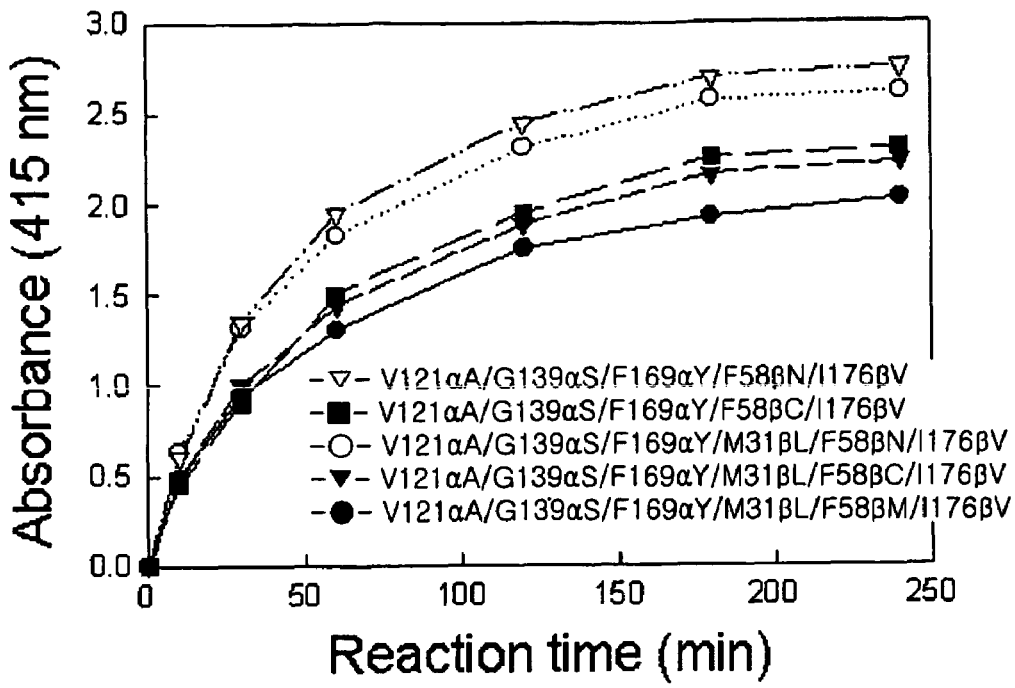
FIG. 8: comparison of the reactivities toward CPC of V121αA/G139αS/F169αY/F58βN/I176βV fivefold CPC acylase mutant (-∇-, mF58), V121αA/G139αS/F169αY/F58βC/I176βV fivefold CPC acylase mutant (-■-), V121αA/G139αS/F169αY/M31βL/F58βN/I176βV sixfold CPC acylase mutant (-○-, TnS5αβ), V121αA/G139αS/F169αY/M31βL/F58βC/I176βV sixfold CPC acylase mutant (-▼-) and V121αA/G139αS/F169αY/M31βL/F58βM/I176βV sixfold CPC acylase mutant (-●-, TnS5)

The enzyme reactivity to CPC was measured by using the crude enzyme solution of each mutant according to the same method as described in Example <1-1-2>. As a result, it has been confirmed that the mutant having a substitution of F58βM by asparagine in TnS5αβ sixfold mutant shows the considerably increased reactivity to CPC and the mutant having a reverse mutation of M31βL into methionine in TnS5αβ sixfold mutant more efficiently produces 7-ACA from CPC although its specific activity decreases somewhat (FIG. 8). From these results, the present invention has selected V121αA/G139αS/F169αY/F58βN/I176βV fivefold mutant (mF58) having a further increased reactivity to CPC than TnS5αβ sixfold mutant (FIG. 5).

<1-4-2> Preparation of Val121α/Gly139α/Phe58β/Ile176β Fourfold Mutant

The present invention has replaced Phe169α by tyrosine in M31βL/F58βM/H70βS triple mutant to further increase the specific reactivity of CPC acylase mutant for CPC in Example <1-1-5>. Meanwhile, H70βS residue in F169αY/M31βL/F58βM/H70βS/I176βV fivefold mutant was subjected to a reverse mutagenesis into histidine in Example <1-2-1> to reduce the end-product inhibition by 7-ACA, and M31βL residue in V121αA/G139αS/F169αY/M31βL/F58βM/I176βV sixfold mutant was also subjected to a reverse mutagenesis into a wild-type residue, methionine in Example <1-4-1>. Further, F58βM mutated residue and I176βresidue in V121αA/G139αS/F169αY/F58βM/I176βV fivefold mutant were replaced by asparagine and valine, respectively. Thus, V121αA/G139αS/F58βN/I176βV fourfold mutant (F169) was prepared by a reverse mutagenesis of F169αY mutated residue into a wild-type residue, phenylalanine (FIG. 5). V121αA/G139αS/F58βN/I176βV fourfold mutant was prepared by the same method for preparing M31βL/F58βM/H70βS triple mutant DNA as described in Example <1-1-4> except that V121αA/G139αS/F169αY/F58βN/I176βV fivefold mutant DNA as a template and F169α-F primer (SEQ ID NO: 45) and F169α-R primer (SEQ ID NO: 46) were employed for PCR.

Figure 9:
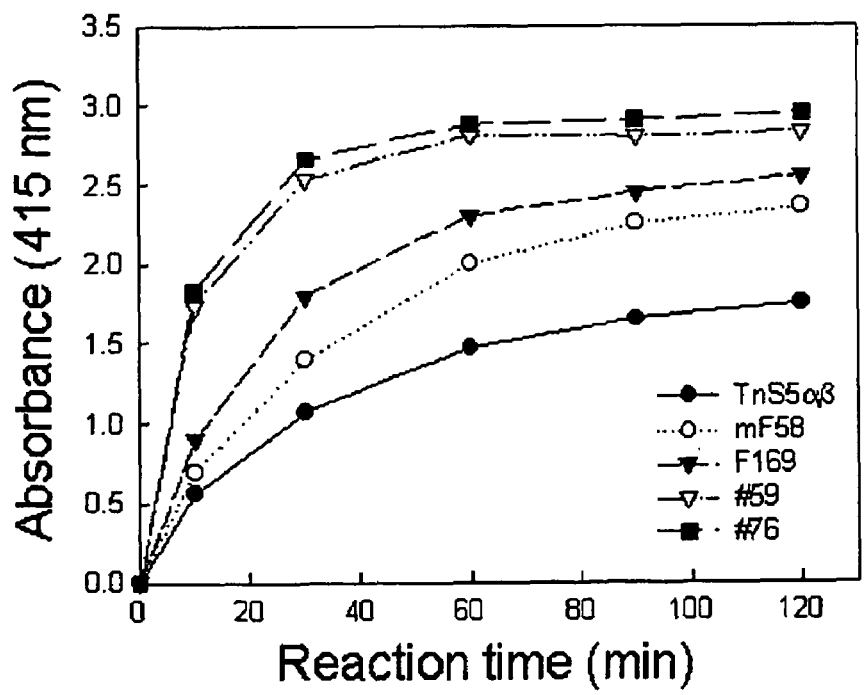
FIG. 9: comparison of the reactivities toward CPC of V121αA/G139αS/F58βN/I176βV fourfold CPC acylase mutant (-▼-, F169), V121αA/G139αS/F58βN/I75βT/I176βV fivefold CPC acylase mutant (-▼-, #59), V121αA/G139αS/F58βN/I176βV/S471βC fivefold CPC acylase mutant (-■-, #76), V121αA/G139αS/F169αY/F58βN/I176βV fivefold CPC acylase mutant (-○-, mF58) and V121αA/G139αS/F169αY/M31βL/F58βN/I176βV sixfold CPC acylase mutant (-●-, TnS5αβ)

The reactivity of V121αA/G139αS/F58βN/I176βV fourfold mutant to CPC was measured by using the crude enzyme solution of mutant enzyme according to the same method as described in Example <1-1-2>. As a result, it has been confirmed that the reverse mutation of F169αY into a wild-type residue, phenylalanine in V121αA/G139αS/F169αY/F58βN/I176βV fivefold mutant further increases the reactivity of CPC acylase mutant to CPC (FIG. 9).

<1-4-3> Preparation of Val121α/Gly139α/Phe58β/Ile75β/Ile176β and Val121α/Gly139α/Phe58β/Ile176β/Ser471β Fivefold Mutants To further increase the reactivity of V121αA/G139αS/F58βN/I176βV fourfold mutant to CPC, V121αA/G139αS/F58βN/I176βV fourfold mutant was subjected to error-prone PCR to construct a random mutant library. A mutant showing the further increased reactivity to CPC than V121αA/G139αS/F58βN/I176βV fourfold mutant was screened from the random mutant library constructed above. At this time, the reaction condition of error-prone PCR, the methods for preparing said mutant library and screening the mutant therefrom were the same as described in Example <1-2-2> except that when the mutant showing the further increased reactivity to CPC was screened from the mutant library, 5 mM 7-ACA (final concentration) was added to the reaction mixture.

As a result of screening about 15,000 colonies from said random mutant library, 2 mutants (#59 and #76) showing the higher absorbance value than V121αA/G139αS/F58βN/I176βV fourfold mutant used as a template for a random mutagenesis were selected. It has been confirmed from the results of sequence analysis that #59 mutant has the substitution of Ile75β by threonine (V121αA/G139αS/F58βN/I75βT/I176βV fivefold mutant) and #76 mutant, the substitution of Ser471β by cysteine (V121αA/G139αS/F58βN/ I176βV/S471βC fivefold mutant) (FIG. 5).

Further, the reactivity of #59 and #76 mutants to CPC were measured by using the crude enzyme solution of each mutant according to the same method as described in Example <1-1-2>. As a result, it has been confirmed that the reactivity of #59 and #76 mutants to CPC are higher than that of V121αA/ G139αS/F58βN/I176βV fourfold mutant (F169) (FIG. 9).

<1-4-4> Preparation of Val121α/Gly139α/Phe58β/Ile75β/ Ile176β/Ser471β Sixfold Mutant It has been confirmed above that the reactivity to CPC is increased by introducing Ile75βT or S471βC mutation into V121αA/G139αS/F58βN/I176βV fourfold mutant. Therefore, to additionally increase the reactivity to CPC, the present invention prepared V121αA/G139αS/F58βN/I75βT/ I176βV/S471βC sixfold mutant by introducing Ile75βT mutation of #59 mutant into #76 mutant (FIG. 5). The sixfold mutant of the present invention was prepared by the same method as described in Example <1-1-4> except that #76 mutant DNA as a template and 175βT-F primer (SEQ ID NO: 43) and 175βT-R primer (SEQ ID NO: 44) were employed for the PCR amplification. The present invention has designated the CPC acylase mutant gene encoding V121αA/G139αS/ F58βN/I75βT/I176βV/S471βC sixfold mutant as S12.

Figure 10A:
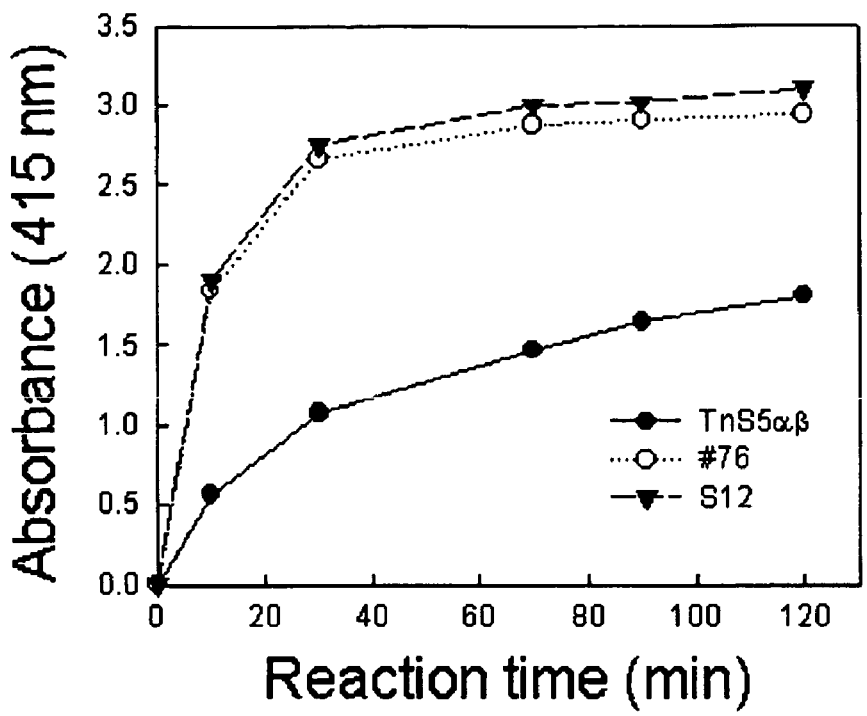
FIGS. 10a and 10b: comparison of the reactivities to CPC (A) and the end-product inhibition by 7-ACA (B) observed for V121αA/G139αS/F58βN/I75βT/I176βV/S471βC sixfold CPC acylase mutant (-▼-, S12) with those observed for V121αA/G139αS/F169αY/M31βL/F58βN/I176βV sixfold CPC acylase mutant (-●-, TnS5αβ) and V121αA/G139αS/F58βN/I176βV/S471βC sixfold CPC acylase mutant (-○-, #76)
Figure 10B:
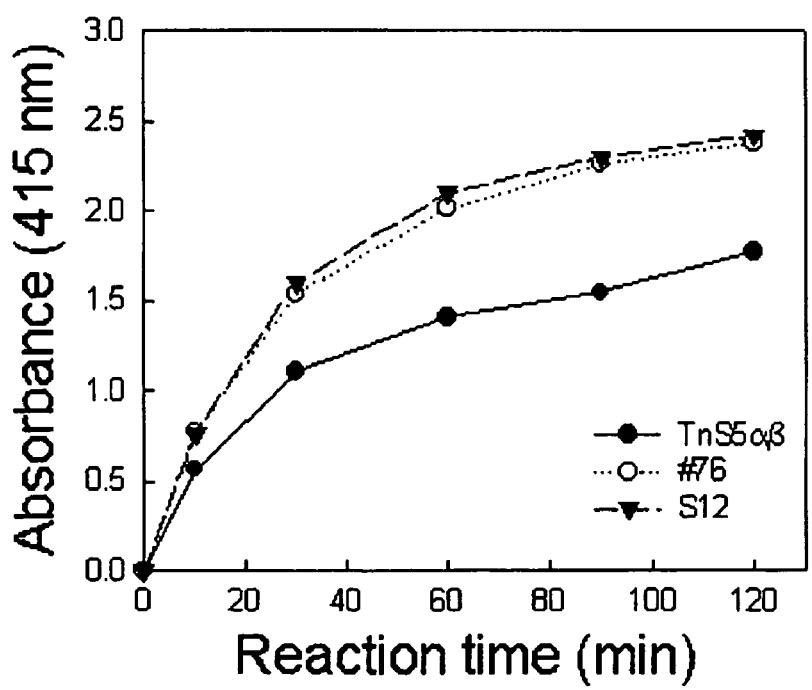

The reactivity of V121αA/G139αS/F58βN/I75βT/ I176βV/S471βC sixfold mutant to CPC was measured by using the crude enzyme solution of sixfold mutant according to the same method as described in Example <1-1-2>. As a result, it has been confirmed that the reactivity of V121αA/ G139αS/F58βN/I75βT/I176βV/S471βC sixfold mutant (S12) to CPC is higher than that of #76 mutant (V121αA/ G139αS/F58βN/I176βV/SβC fivefold mutant) (FIG. 10).

EXAMPLE 2

Purification of CPC Acylase Mutant and Analysis of its Reaction Property

<2-1> Purification of CPC Acylase Mutant Having an Increased Specific Activity to CPC.

*E. coli* MC1061 transformant containing the recombinant plasmid introduced with the wild-type or the inventive CPC acylase mutant gene was cultivated in 1 l of a terrific broth (1.2% Bacto-Trypton, 2.4% Yeast Extract, 0.4% glycerol, 0.17 M $KH_2PO_4$, 0.72 M $K_2HPO_4$) containing 25/g/ml of chloramphenicol at 30° C. for 16 hr to obtain a pre-culture solution. 10 ml of the pre-culture solution was inoculated into the same medium, and then, cultured at 25° C., 200 rpm for 48 hr with vigorous shaking. The culture solution was subjected to centrifugation at 4° C., 8,000 rpm for 10 min to separate a precipitate, and the precipitate washed twice with 20 mM Tris-HCl buffer solution (pH 8.0). The precipitate was suspended in 100 mg of the same buffer solution. This suspension was subjected to ultra sonication at 4° C. for 20 min to destruct a cell wall and centrifugation at 4° C., 15,000 rpm for 20 min to remove insoluble materials and cell debris, which results in obtaining a supernatant used as a crude enzyme solution in the following.

Ammonium sulfate was added to the crude enzyme solution to be adjusted its final saturation rate to 30% and the reaction mixture was stirred at 4° C. for 1 hr to saturate. After then, the reaction mixture was subjected to centrifugation at 4° C., 12,000 rpm for 15 min to remove a precipitate and ammonium sulfate was added to the supernatant to be adjusted a final saturation rate to 60%. The reaction mixture was stirred at 4° C. for 1 hr to saturate and subjected to centrifugation at 4° C., 12,000 rpm for 15 min to recover a precipitate. The precipitate was suspended in 20 mM Tris-HCl buffer solution (pH 8.0) and subjected to dialysis with 20 mM Tris-HCl buffer solution (pH 8.0) containing 50 mM NaCl for overnight.

The protein solution obtained by dialysis was subjected to DEAE-sepharose anion exchange column chromatography (5×18.5 cm) equilibrated with 20 mM Tris-HCl buffer solution (pH 8.0) containing 50 mM NaCl and the column washed with triple volume of the same buffer solution to remove protein molecules that do not absorb thereto. The absorbed protein was eluted by gradually increasing the concentration of NaCl ranging from 50 to 200 mM. The fraction showing a CPC acylase activity was collected and concentrated with a polyethylene glycol (M.W. 20,000) in a dialysis bag. The concentrated protein was subjected to dialysis with 20 mM Tris-HCl buffer solution (pH 8.0) containing 25% ammonium sulfate.

The diffusate obtained above was subjected to Phenyl-Toyoperl column chromatography (2.5×6 cm) equilibrated with 20 mM Tris-HCl buffer solution (pH 8.0) containing 25% ammonium sulfate to absorb the protein to the column, and the absorbed protein was eluted by gradually decreasing the concentration of ammonium sulfate ranging from 25 to 0%. After confirming the CPC acylase activity of each fraction, the fraction having the enzyme activity was recovered, concentrated with a polyethylene glycol and subjected to dialysis with 20 mM Tris-HCl buffer solution (pH 8.0), to purify the wild-type and the inventive CPC acylase mutant.

The enzyme activity was measured by the same method as described in Example <1-1-2>.

<2-2> Analysis of Physical Property and Reaction Feature of Wild-Type CPC Acylase The wild-type CPC acylase was purified from *E. coli* transformant containing pBCPC or pBSEM plasmid prepared in Example <1-1-2> according to the same method as described in Example <2-1>. As a result of analyzing the physical property and reaction feature of pBCPC plasmid derived wild-type CPC acylase (AcyII) and pBSEM plasmid derived wild-type CPC acylase (Sem), respectively, they showed the same physical property (e.g., molecular weight) and reaction feature (e.g., specific activity, optimal temperature, optimal pH).

Figure 11A:
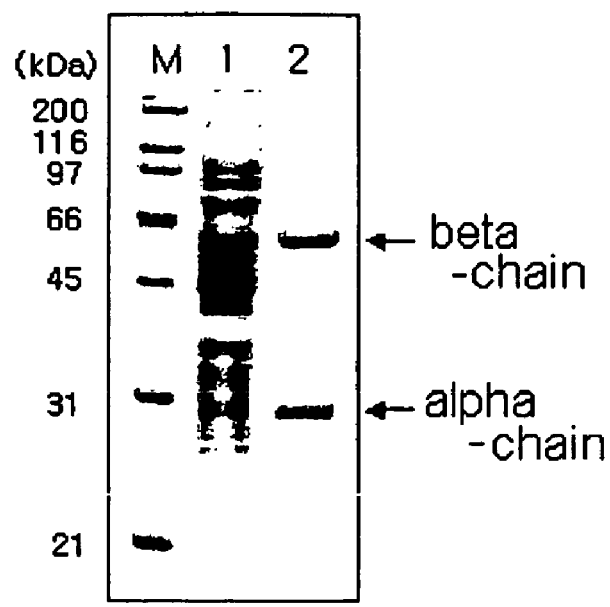
FIGS. 11a to 11c: the molecular weight of *Pseudomonas* sp. SE83 derived wild-type CPC acylase.
Figure 11B:
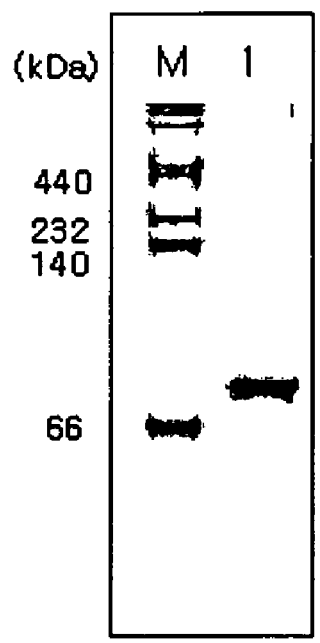
Figure 11C:
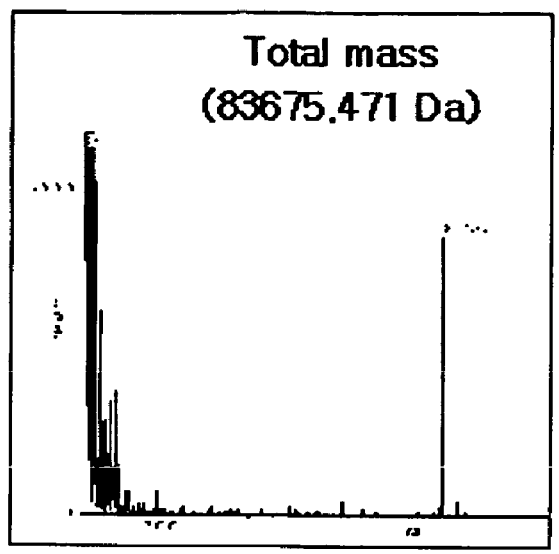

Further, the active fraction of wild-type CPC acylase obtained in Example <2-1> was subjected to non-denaturing PAGE and Coomasie blue staining. As a result, a single band was detected at a position corresponding to the molecular weight of about 83 kDa, which means that the wild-type CPC acylase was purely purified (FIGS. 11a to 11c). Together with the result of non-denaturing PAGE, MALDI-TOF mass spectrophotometry analysis confirmed that the molecular weight of purified enzyme (that is, the active CPC acylase) is about 83 kDa. Furthermore, about 25 kDa of band corresponding to α-subunit and about 58 kDa of band corresponding to β-subunit were detected by denaturing SDS-PAGE. From these results, it has been confirmed that the inventive CPC acylase mutant is a dimer consisting of about 25 kDa of α-subunit and about 58 kDa of β-subunit one by one.

α- and β-subunits were purified from the denaturing SDS-PAGE gel, respectively, and the molecular weight of each subunit fragment was measured by MALDI-TOF mass spectrophotometry analysis. As a result, it has been supposed that the wild-type CPC acylase (AcyII) derived from pBCPC plasmid is separated into about 25 kDa of α-subunit and about 58 kDa of β-subunit by removing a spacer peptide consisting of 9 amino acids via a self-digestion occurred at two positions between the 230$^{th}$ and the 231$^{st}$ amino acids, and the 239$^{th}$ and the 240$^{th}$ amino acids in the amino acid sequence of SEQ ID NO: 2, respectively.

As a result of examining the specific activity of wild-type CPC acylase, the wild-type CPC acylase showed about 23.1 unit/mg protein of the specific activity to GL-7-ACA and about 0.33 unit/mg protein of the specific activity to CPC. Therefore, it has been known that the *Pseudomonas* sp. SE83 derived AcyII shows the specific activity to CPC corresponding to only about 1.4% of that to GL-7-ACA.

After performing the enzyme reaction according to the same method as described in Example <1-1-2>, a kinetic parameter of the purified enzyme was determined by Lineweaver-Burk plot method. As a result, Km, Kcat and a catalytic efficiency (that is, Kcat/Km) of the wild-type CPC acylase AcyII were 50 mM, 0.9/sec and 0.02/sec/mM, respectively.

Further, as a result of examining the optimal reaction temperature and pH of the wild-type CPC acylase AcyII, the optimal reaction temperature and pH to CPC were 40° C. and 9.0, respectively.

<2-3> Analysis of Reaction Feature of CPC Acylase Mutant Having an Increased Specific Activity Each CPC acylase mutant was purified from the recombinant *E. coli* transformed with the plasmid containing each CPC acylase mutant gene encoding M31βL/F58βM double mutant, M31βL/F58βM/H70βS triple mutant, F169αY/M31βL/F58βM/H70βS fourfold mutant and F169αY/M31βL/F58βM/H70βS/I176βV fivefold mutant, respectively, according to the same method as described in Example <2-1>.

As a result of analyzing the reaction feature of each purified mutant enzyme, their reaction feature (e.g., optimal temperature and pH) and physical property (e.g., molecular weight) were the same as the wild-type CPC acylase. However, as a result of examining the specific activity of each mutant enzyme, the specific activity of each mutant to CPC gradually increased as a mutagenesis makes steady progress (Table 2). From these successive mutagenesis, F169αY/M31βL/F58βM/H70βS/I176βV fivefold CPC acylase mutant showing the increased specific activity of about 11.2-fold higher than the wild-type CPC acylase to CPC was obtained.

TABLE 2

| Mutant enzyme | Relative activity to CPC (fold) |
| --- | --- |
| Wild-type | 1.0 |
| M31βL/F58βM | 1.2 |
| M31βL/F58βM/H70βS | 5.2 |
| F169αY/M31βL/F58βM/H70βS | 7.3 |
| F169αY/M31βL/F58βM/H70βS/I176βV | 11.2 |

After performing the enzyme reaction according to the same method as described in Example <1-1-2>, a kinetic parameter of F169αY/M31βL/F58βM/H70βS/I176βV fivefold mutant enzyme was determined by Lineweaver-Burk plot method. As a result, Km, Kcat and Kcat/Km were 8 mM, 2.4/sec and 0.30/sec/mM, respectively. F169αY/M31βL/F58βM/H70βS/I176βV fivefold mutant showed about 6.3-fold lower Km value and about 15-fold higher reaction efficiency to CPC as is compared with the wild-type enzyme. From these results, it has been confirmed that the inventive CPC acylase mutant obtained by a series of site-directed mutagenesis based on the tertiary structural information of CAD has an increased binding affinity and a specific activity to CPC.

<2-4> Purification of CPC Acylase Mutant Having an Increased Reactivity to CPC and Analysis of Reaction Feature Thereof.

Each sixfold CPC acylase mutant was purified from the recombinant *E. coli* transformed with the plasmid containing the CPC acylase mutant gene (TnS5αβ) encoding V121αA/G139αS/F169αY/M31βL/F58βM/I176βV sixfold mutant of Example <1-3> or the CPC acylase mutant gene (S12) encoding V121αA/G139αS/F58βN/I75βT/I176βV/S471βC sixfold mutant of Example <1-4-4> according to the same method as described in Example <2-1>.

As a result of analyzing the reaction feature of each purified mutant enzyme TnS5αβ and S12, their reaction feature (e.g., optimal temperature and pH) and physical property (e.g., molecular weight) were the same as the wild-type CPC acylase.

To examine the specific activity to CPC and the end-product inhibition by 7-ACA of each CPC acylase mutant, the enzyme reaction was performed according to the same method as described in Example <1-1-2> except that pH of the reaction mixture was adjusted to 8.5. As a result, the specific activity of TnS5αβ and S12 mutant enzymes to CPC were 1.5 unit/mg protein and 5.8 unit/mg protein, respectively, which corresponds to 2.3- and 8.5-fold higher than that of the wild-type CPC acylase. Further, as a result measuring the inhibition constant (Ki) by 7-ACA of S12 mutant enzyme, while Ki value of the wild-type enzyme was 0.4 mM, Ki value of S12 mutant enzyme, 1.9 mM, which means that the end-product inhibition by 7-ACA of S12 mutant enzyme was significantly decreased as compared with that of the wild-type enzyme. From these results, it has been confirmed that the inventive S12 mutant enzyme (V121αA/G139αS/F58βN/I75βT/I176βV/S471βC sixfold mutant) shows the increased specific activity to CPC but the decreased end-product inhibition by 7-ACA.

EXAMPLE 3

Production of CPC Acylase Mutant in *E. coli*

<3-1> Production of CPC Acylase Mutant Using pBC KS(+) Vector

V121αA/G139αS/F169αY/M31βL/F58βM/I176βV sixfold CPC acylase mutant encoding genes TnS and TnS5αβ, and V121αA/G139αS/F58βN/I75βT/I176βV/S471βC sixfold CPC acylase mutant encoding gene S12 were inserted into pBC KS(+) vector to obtain pBC-TnS5, pBC-TnS5αβ and pBC-S12 recombinant plasmids, respectively, and *E. coli* MC1061 was transformed with each resulting recombinant plasmid.

Each *E. coli* transformant was cultivated in 50 ml of a LB broth containing 25 μg/ml of chloramphenicol at 25° C., 200 rpm for 48 hr with vigorous shaking and the productivity of CPC acylase was measured by using the crude enzyme solution prepared from the culture solution according to the same method as described in Example <1-1-2>. At this time, the recombinant plasmids pBSEM and pBCPC containing the wild-type acylase encoding gene acyII and sem, respectively, were used as a control. As a result, *E. coli* trasnformant containing pBC-S12 plasmid showed the maximum productivity of CPC acylase at a level of 712 unit/Q

TABLE 3

| The formation pattern of CPC acylase | Plasmid (CPC acylase) | The productivity of CPC acylase (unit/l) |
|---|---|---|
| Respective expression of each subunit | pBSEM (wild-type) | 11 |
| | pBC-TnS5 (TnS5 sixfold mutant) | 78 |
| Self-digestion | pBCPC (wild-type) | 97 |
| | pBC-TnS5αβ (TnS5αβ sixfold mutant) | 162 |
| | pBC-S12 (S12 sixfold mutant) | 712 |

<3-2> Production of CPC acylase mutant using pET29-a(+) vector

<3-2-1> Preparation of pET29-TnS5αβ and pET29-S12 plasmids

The recombinant plasmids pBC-TnS5αβ and pBC-S12 were subjected to the PCR amplification using pET29-F primer (SEQ ID NO: 40) and pET29-R primer (SEQ ID NO: 41), respectively, to obtain 2.5 kb of PCR product each. After the PCR amplification, the PCR product was digested with XbaI/XhoI and purified with a purification kit (QIAEX II Gel Extraction Kit; Qiagen, Germany), to obtain an insert DNA. Further, pET29-a(+) vector DNA (Novagen, USA) was digested with XbaI/XhoI and subjected to dephosphorylation with CIP, to obtain a vector DNA. The insert DNA and vector DNA were subjected to ligation using T4 DNA ligase (Roche, Germany) at 16° C. for 16 hr and transformed to E. coli MC1061 strain by electrophoration. The E. coli strain was spread onto a LB agar plate containing 20 μg/ml of kanamycin and cultured at 30° C. incubator for overnight to select a transformant containing the mutant gene. The plasmid was purified from the selected transformant and the nucleotide sequence of insert DNA was analyzed, to obtain pET29-TnS5αβ and pET29-S12 plasmids.

<3-2-2> Production of CPC acylase mutant by E. coli transformant containing pET29-TnS5αβ or pET29-S12 plasmid Each of pET29-TnS5αβ and pET29-S12 plasmids was transformed into E. coli BL21(DE3) by electrophoration to prepare the recombinant E. coli containing pET29-TnS5αβ and pET29-S12 plasmid, respectively, and the productivity of sixfold CPC acylase mutant in each recombinant E. coli was measured. The TnS5αβ and S12 CPC acylase mutant gene in these recombinant plasmids was transcribed by the action of T7 promoter which is under the control of LacI operator existed on pET29-a(+) vector.

The recombinant E. coli containing pET-TnS5αβ plasmid was inoculated in 3 mg of a LB broth containing 20 μg/ml of kanamycin and cultivated at 30° C., 200 rpm for 16 hr with vigorous shaking. 50 μl of the culture solution was transferred to 50 ml of a new LB broth containing 20 μg/ml of kanamycin and 0, 0.02, 0.2 and 2% lactose each and cultured at 25° C., 200 rpm for 80 hr with vigorous shaking. At this time, to measure the productivity of CPC acylase mutant according to the time course of cultivation, 5 μl of the culture broth was taken from the culture flask at 24, 36, 48, 72 and 80 hr during the cultivation, respectively. Each culture solution was subjected to centrifugation at 4° C., 8,000 rpm for 10 min to separate a precipitate and the precipitate washed twice with 0.1 M Tris-HCl buffer solution (pH 8.0). After the precipitate was suspended in 500 μl of the same buffer solution, it was subjected to ultra sonication at 4° C. for 1 min and centrifugation at 4° C., 15,000 rpm for 20 min to separate a supernatant, which can be used as a crude enzyme solution of the sixfold CPC acylase mutant. The activity of sixfold CPC acylase mutant to CPC was measured using said crude enzyme solution according to the same method as described in Example <1-1-2>.

Since IPTG generally used as an inducer for a high expression of foreign gene in an expression system of pET29 vector and E. coli BL21(DE3) is too expensive, it is difficult to apply IPTG to the industrial scale of cultivation. Thus, the present invention has employed a low-priced inducer, lactose (DIFCO, USA) instead of IPTG for the mass-production of CPC acylase mutant. Further, it has been generally known in the art that the expression system of pET29 vector and E. coli BL21 (DE3) highly expresses the foreign gene within a short period by culturing a transformant for a fixed time without an inducer at the early stage of cultivation to propagate it and further culturing with the addition of inducer at a fixed point. However, since it was confirmed that the inducible expression method for producing the CPC acylase described above generated a large quantity of inactive polypeptide as a by-product, the present invention cultured the E. coli transformant with the addition of lactose at the early stage of cultivation to induce a constitutive expression. As a result, in case of culturing with 2% lactose, the productivity of CPC acylase was increased by the action of lactose as an inducer according to the time course of cultivation (Table 4).

In addition, each crude enzyme solution was prepared from three culture broth containing a different concentration of lactose (0.02, 0.2 and 2%) taken at 48 hr after the cultivation and subjected to denaturing SDS-PAGE (12% SDS-polyacrylamide gel) to examine the expression pattern of a protein. As a result, the CPC acylase mutant was produced in a large quantity in case of culturing with 2% lactose (FIG. 12). Further, there was no inactive precursor band corresponding to the molecular weight of about 83 kDa, which confirms that most of the inactive precursor form convert into the active form of CPC acylase by an efficient self-digestion.

TABLE 4

| Concentration of lactose | Period of cultivation (hr) | Cell growth ($OD_{600}$) | Productivity of CPC acylase mutant (unit/l) |
|---|---|---|---|
| 0% | 24 | 6.8 | 5 |
| | 36 | 6.9 | 6 |
| | 48 | 5.8 | 3 |
| 0.02% | 24 | 4.7 | 35 |
| | 36 | 4.2 | 36 |
| | 48 | 3.5 | 32 |
| 0.2% | 24 | 5.8 | 71 |
| | 36 | 5.2 | 72 |
| | 48 | 4.4 | 64 |
| 2% | 24 | 5.7 | 118 |
| | 36 | 7.8 | 132 |
| | 48 | 9.5 | 168 |
| | 60 | 11.2 | 304 |
| | 72 | 11.5 | 334 |
| | 80 | 12.2 | 312 |

Further, the productivity of CPC acylase by S12 mutant enzyme in the E. coli BL21(DE3) transformant containing pET29-S12 recombinant plasmid was measured according to the same method as described above except that 50 mg of a LB broth containing 20 μg/ml of kanamycin and 2% lactose was employed for a main cultivation and the E. coli transformant was cultured at 25° C., 200 rpm for 72 hr with vigorous shaking. As a result, the productivity of V121αA/G139αS/F58βN/I75βT/I176βV/S471βC sixfold CPC acylase mutant (S12) was 1,207 unit/l.

E. coli BL21(DE3) transformed with pET29-S12 plasmid containing the inventive V121αA/G139αS/F58βN/I75βT/

I176βV/S471βC sixfold CPC acylase mutant gene S12 has been designated *E. coli* BL21(DE3)/pET-S12 which was deposited on Jul. 30, 2003 with the Korean Collection for Type Cultures (KCTC) (Address: Korea Research Institute of Bioscience and Biotechnology (KRIBB), #52, Oun-dong, Yusong-ku, Taejon, 305-333, Republic of Korea) under the accession number KCTC 10503BP, in accordance with the terms of Budapest Treaty on the International Recognition of the Deposit of Microorganism for the Purpose of Patent Procedure.

EXAMPLE 4

One-Step Conversion of CPC into 7-ACA Using CPC Acylase Mutant

*E. coli* BL21(DE3) transformant containing each one of pET29-TnS5αβ and pET29-S12 plasmids of Example <3-2> was cultivated in 5 l of a LB broth containing 20 μg/ml of kanamycin and 2% lactose at 25° C., 200 rpm for 72 hr with vigorous shaking. Further, *E. coli* MC1061(pBCPC) containing the wild-type CPC acylase gene was also cultivated in 10 l of a LB broth containing 25 μg/ml of chloramphenicol at 25° C., 200 rpm for 48 hr with vigorous shaking. After then, the wild-type CPC acylase, TnS5αβ and S12 CPC acylase mutants were purified from each culture broth according to the same method as described in Example <2-1>, respectively. The purified protein obtained above was subjected to dialysis with 50 mM phosphate buffer solution (pH 8.5), and the diffusate obtained by dialysis was used for a CPC conversion reaction.

After CPC was dissolved in 50 mM phosphate buffer solution (pH 8.5) at a final concentration of 50 mM, the purified enzyme solution dissolved in the same buffer solution was added to the CPC solution obtained above at a final concentration of 5 unit/mg to prepare 50 mg of the reaction mixture. The reaction mixture was stirred at 25° C. for 1 hr to induce a CPC conversion reaction. At this time, in order to prevent pH of the reaction mixture from decreasing during the conversion reaction, when pH of the reaction mixture was reached to 8.4, 0.2 N NaOH solution was automatically injected to the reaction mixture by a pH regulator to constantly maintain pH of the reaction mixture at 8.5. 100 μl of the reaction mixture was taken from at a fixed time during the conversion reaction and immediately subjected to a HPLC analysis to quantify the amount of CPC and 7-ACA in the reaction mixture. For the HPLC analysis, Symmetry C18 column (Waters, USA) and the mixture (90:10) of 20 mM ammonium acetate buffer solution (pH 5.0) and acetonitrile as a mobile phase were employed. In addition, the flow rate of mobile phase was 0.6 ml/min, the sample (20 μl) to be injected was prepared by appropriately diluting the reaction mixture with 50 mM phosphate buffer solution (pH 8.5), and its absorbance was detected at UV 250 nm.

As a result, while the wild-type CPC acylase showed 60% level of CPC conversion rate under the reaction condition described above, TnS5αβ and S12 CPC acylase mutants of the present invention, 86% and 98% level of CPC conversion rate, respectively (FIG. 13). In particular, the inventive S12 CPC acylase mutant efficiently converted CPC into 7-ACA at a high level of 7-ACA yield (90% or more) (FIGS. 13 and 14).

While the embodiments of the subject invention have been described and illustrated, it is obvious that various changes and modifications can be made therein without departing from the spirit of the present invention which should be limited only by the scope of the appended claims.

What is claimed is:

1. A CPC acylase mutant, wherein at least one amino acid selected from the group consisting of Val121α, Gly 139α and Phe 169α of CPC acylase α-subunit of SEQ ID NO: 4 and Phe 58β, His 70β, Ile 75β, Ile 176β and Ser 471β of CPC acylase β-subunit of SEQ ID NO: 5 is replaced by another amino acid.

2. The CPC acylase mutant according to claim 1, wherein:
Val 121α is replaced by alanine;
Gly 139α is replaced by serine;
Phe 169α is replaced by tyrosine;
Phe 58β is replaced by alanine, methionine, leucine, valine, cysteine or asparagine;
His 70β is replaced by serine or leucine;
Ile 75β is replaced by threonine;
Ile 176β is replaced by valine; or
Ser 471β is replaced by cysteine.

3. The CPC acylase mutant according to claim 2, wherein Phe 58β is replaced by alanine, methionine, leucine, valine, cysteine or asparagine, and further Met 31β is replaced by leucine.

4. The CPC acylase mutant according to claim 3, wherein His 70β is replaced by serine or leucine.

5. The CPC acylase mutant according to claim 4, wherein Phe 169α is replaced by tyrosine.

6. The CPC acylase mutant according to claim 5, wherein Ile 176β is replaced by valine.

7. The CPC acylase mutant according to claim 3, wherein Phe 169α is replaced by tyrosine and Ile 176β is further replaced by valine.

8. The CPC acylase mutant according to claim 7, wherein Val 121α is replaced by alanine.

9. The CPC acylase mutant according to claim 7, wherein Gly 139α is replaced by serine.

10. The CPC acylase mutant according to claim 7, wherein Val 121α is replaced by alanine and Gly 139α is further replaced by serine.

11. The CPC acylase mutant according to claim 2, wherein Val 121α Is replaced by alanine; Gly 139α is replaced by serine; Phe 58β is replaced by alanine, methionine, leucine, valine, cysteine or asparagine; and Ile 176β is replaced by valine.

12. The CPC acylase mutant according to claim 11, wherein Phe 169α is replaced by tyrosine.

13. The CPC acylase mutant according to claim 11, wherein He 75β is replaced by threonine.

14. The CPC acylase mutant according to claim 11, wherein Ser 471β is replaced by cysteine.

15. The CPC acylase mutant according to claim 11, wherein Ile 75β is replaced by threonine and Ser 471β is replaced by cysteine.

16. The CPC acylase mutant according to claim 15, which has an amino acid sequence comprising CPC acylase α-subunit of SEQ ID NO: 7 and CPC acylase 1-subunit of SEQ ID NO: 8.

17. A composition comprising the CPC acylase mutant of claim 1 for preparing 7-ACA by a one-step enzymatic method.

* * * * *